(12) United States Patent
Dubois et al.

(10) Patent No.: US 7,763,636 B2
(45) Date of Patent: Jul. 27, 2010

(54) N-(ARYLALKYL)-1H-PYRROLOPYRIDINE-2-CARBOXAMIDE DERIVATIVES, PREPARATION AND THERAPEUTIC USE THEREOF

(75) Inventors: Laurent Dubois, Le Plessis-Robinson (FR); Yannick Evanno, Dannemois (FR); Andre Malanda, Villejust (FR)

(73) Assignee: Sanofi-Aventis, Paris (FR)

( * ) Notice: Subject to any disclaimer, the term of this patent is extended or adjusted under 35 U.S.C. 154(b) by 395 days.

(21) Appl. No.: 11/970,886

(22) Filed: Jan. 8, 2008

(65) Prior Publication Data

US 2008/0125459 A1 May 29, 2008

Related U.S. Application Data

(63) Continuation of application No. PCT/FR2006/001767, filed on Jul. 19, 2006.

(30) Foreign Application Priority Data

Jul. 22, 2005 (FR) .................................. 05 07804

(51) Int. Cl.
C07D 471/02 (2006.01)
A61K 31/4745 (2006.01)

(52) U.S. Cl. ...................................... 514/300; 546/113
(58) Field of Classification Search ................ 546/113; 514/300
See application file for complete search history.

(56) References Cited

U.S. PATENT DOCUMENTS

| 2005/0165049 A1 | 7/2005 | Hulme et al. | |
| 2009/0042873 A1* | 2/2009 | Dubois et al. | 514/230.2 |

FOREIGN PATENT DOCUMENTS

| EP | 1535922 | 6/2005 |
| WO | WO 01/64639 | 9/2001 |
| WO | WO 03/068749 | 8/2003 |
| WO | WO 2004/072069 | 8/2004 |

* cited by examiner

*Primary Examiner*—D. Margaret Seaman
*Assistant Examiner*—Niloofar Rahmani
(74) *Attorney, Agent, or Firm*—Balaram Gupta

(57) ABSTRACT

The invention concerns compounds of general formula (I), wherein n, the pyrrolopyridine ring, X, $Z_1$, $Z_2$, $Z_3$, $Z_4$, $Z_5$ and W are as defined herein.

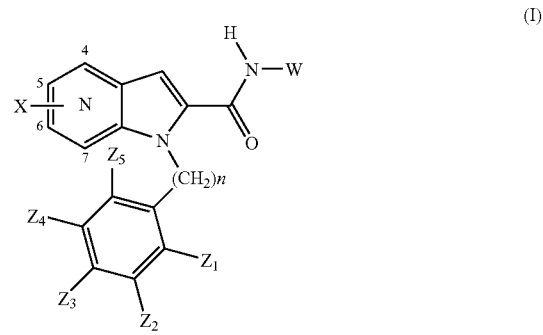

The invention also concerns a method for preparing said compounds and their therapeutic use.

22 Claims, No Drawings

N-(ARYLALKYL)-1H-PYRROLOPYRIDINE-2-CARBOXAMIDE DERIVATIVES, PREPARATION AND THERAPEUTIC USE THEREOF

This application is a continuation of International application No. PCT/FR2006/001,767, filed Jul. 19, 2006, which is incorporated herein by reference in its entirety; which claims the benefit of priority of French Patent Application No. 05/07,804, filed Jul. 22, 2005.

The invention relates to compounds derived from N-(arylalkyl)-1H-pyrrolopyridine-2-carboxamides, which show in vitro and in vivo antagonist activity towards receptors of TRPV1 (or VR1) type.

A first subject of the invention concerns compounds corresponding to the general formula (I) below.

Another subject of the invention concerns processes for preparing the compounds of general formula (I).

Another subject of the invention concerns the use of the compounds of general formula (I) especially in medicaments or in pharmaceutical compositions.

The compounds of the invention correspond to the general formula (I):

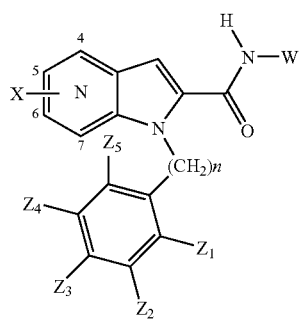

(I)

in which n is equal to 0, 1, 2 or 3;

the pyrrolopyridine nucleus is a pyrrolo[3,2-b]pyridine group, a pyrrolo[3,2-c]pyridine group, a pyrrolo[2,3-c]pyridine group or a pyrrolo[2,3-b]pyridine group; the pyrrolopyridine nucleus being optionally substituted in the carbon position 4, 5, 6 and/or 7 with one or more substituents X, which may be identical or different, chosen from a halogen atom and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_1$-$C_6$-fluoroalkoxyl, cyano, C(O)$NR_1R_2$, nitro, $NR_1R_2$, $C_1$-$C_6$-thioalkyl, —S(O)—$C_1$-$C_6$-alkyl, —S(O)$_2$—$C_1$-$C_6$-alkyl, SO$_2NR_1R_2$, $NR_3COR_4$, $NR_3SO_2R_5$ or aryl group, the aryl being optionally substituted with one or more substituents chosen from a halogen and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_1$-$C_6$-fluoroalkoxyl, nitro or cyano group;

$Z_1$, $Z_2$, $Z_3$, $Z_4$ and $Z_5$ represent, independently of each other, a hydrogen or halogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_1$-$C_6$-fluoroalkoxyl, cyano, C(O)$NR_1R_2$, nitro, $NR_1R_2$, $C_1$-$C_6$-thioalkyl, —S(O)—$C_1$-$C_6$-alkyl, —S(O)$_2$—$C_1$-$C_6$-alkyl, SO$_2NR_1R_2$, $NR_3COR_4$, $NR_3SO_2R_5$, aryl-$C_1$-$C_6$-alkylene or aryl group, the aryl and the aryl-$C_1$-$C_6$-alkylene being optionally substituted with one or more substituents chosen from a halogen and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_1$-$C_6$-fluoroalkoxyl, nitro or cyano group;

$R_1$ and $R_2$ represent, independently of each other, a hydrogen atom or a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene or aryl group; or $R_1$ and $R_2$ together forming, with the nitrogen atom that bears them, an azetidine, pyrrolidine, piperidine, azepine, morpholine, thiomorpholine, piperazine, homopiperazine group, this group being optionally substituted with a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene or aryl group;

$R_3$ and $R_4$ represent, independently of each other, a hydrogen atom or a $C_1$-$C_6$-alkyl, aryl-$C_1$-$C_6$-alkylene or aryl group;

$R_5$ represents a $C_1$-$C_6$-alkyl or aryl group;

W represents a fused bicyclic group of formula:

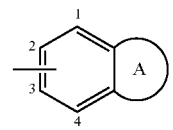

bonded to the nitrogen atom via positions 1, 2, 3 or 4;

A represents a 5- to 7-membered heterocycle comprising from one to three heteroatoms chosen from O, S and N;

the carbon atom(s) of A being optionally substituted with one or more groups chosen from a hydrogen atom and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl, aryl-$C_1$-$C_6$-alkylene, oxo or thio group;

the nitrogen atom(s) of A being optionally substituted with $R_6$ when the nitrogen is adjacent to a carbon atom substituted with an oxo group, or with $R_7$ in the other cases;

$R_6$ represents a hydrogen atom or $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-$C_1$-$C_6$-alkylene or aryl group;

$R_7$ represents a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-$C_1$-$C_6$-alkylene, $C_1$-$C_6$-alkyl-C(O)—, $C_3$-$C_7$-cycloalkyl-$C_1$-$C_3$-alkylene-(CO)—, $C_1$-$C_6$-fluoroalkyl-C(O)—, $C_3$-$C_7$-cycloalkyl-C(O)—, aryl-C(O)—, aryl-$C_1$-$C_6$-alkylene-C(O)—, $C_1$-$C_6$-alkyl-S(O)$_2$—, $C_1$-$C_6$-fluoroalkyl-S(O)$_2$—, $C_3$-$C_7$-cycloalkyl-S(O)$_2$—, $C_3$-$C_7$-cycloalkyl-$C_1$-$C_3$-alkylene-S(O)$_2$—, aryl-S(O)$_2$— or aryl-$C_1$-$C_6$-alkylene-S(O)$_2$— or aryl group.

In the compounds of general formula (I):

the sulfur atom(s) of the heterocycle A may be in oxidized form (S(O) or S(O)$_2$);

the nitrogen atom(s) of the heterocycle A may be in oxidized form (N-oxide);

the nitrogen atom in position 4, 5, 6 or 7 of the pyrrolopyridine may be in oxidized form (N-oxide).

In the context of the invention, examples of group W that may be mentioned include indolinyl, isoindolinyl, indolyl, isoindolyl, benzofuranyl, dihydrobenzofuranyl, benzothiophenyl, dihydrobenzothiophenyl, benzoxazolyl, dihydrobenzoxazolinyl, isobenzofuranyl, dihydroisobenzofuryl, benzimidazolyl, dihydrobenzimidazolyl, indazolyl, benzothiazolyl, isobenzothiazolyl, dihydroisobenzothiazolyl, benzotriazolyl, quinolyl, dihydroquinolyl, tetrahydroquinolyl, isoquinolyl, dihydroisoquinolyl, tetrahydroisoquinolyl, benzoxazinyl, dihydrobenzoxazinyl, benzothiazinyl, dihydrobenzothiazinyl, cinnolinyl, quinazolinyl, dihydroquinazolinyl, tetrahydroquinazolinyl, quinoxalinyl, dihydroquinoxalinyl, tetrahydroquinoxalinyl, phthalazinyl, dihydrophthalazinyl, tetrahydrophthalazinyl, tetrahydrobenz[b]azepinyl, tetrahydrobenz[c]azepinyl, tetrahydrobenz[d]azepinyl, tetrahydrobenzo[b][1,4]diazepinyl, tetrahydrobenzo[e][1,4]diazepinyl, tetrahydrobenzo[b][1,4]oxazepinyl or tetrahydrobenzo[b][1,4]thiazepinyl groups; these groups possibly being substituted as defined in the general formula (I).

Among the compounds of general formula (I) that are subjects of the invention, a first subgroup of compounds consists of the compounds for which n is equal to 1 or 2.

Among the compounds of general formula (I) that are subjects of the invention, a second subgroup of compounds consists of the compounds for which the pyrrolopyridine nucleus is a pyrrolo[3,2-b]pyridine group, a pyrrolo[3,2-c]pyridine group, a pyrrolo[2,3-c]pyridine group or a pyrrolo[2,3-b]pyridine group;

the pyrrolopyridine nucleus being optionally substituted in the carbon position 4, 5, 6 and/or 7 with one or more substituents X, which may be identical or different, chosen from a hydrogen or halogen atom, for example, a fluorine, a bromine or a chlorine, and a $C_1$-$C_6$-alkyl group, for example a methyl, a propyl, an isopropyl, a sec-butyl, a tert-butyl, a pentyl, $C_3$-$C_7$-cycloalkyl, for example a cyclopentyl or a cyclohexyl, $C_1$-$C_6$-fluoroalkyl, for example a trifluoromethyl group, $C_1$-$C_6$-alkoxyl, for example a methoxy or an ethoxy, $C_1$-$C_6$-fluoroalkoxyl, for example a trifluoromethoxy group, nitro, $NR_1R_2$, $C_1$-$C_6$-thioalkyl, for example a thiomethyl, —S(O)—$C_1$-$C_6$-alkyl, —S(O)$_2$—$C_1$-$C_6$-alkyl, for example an —S(O)$_2$—$CH_3$, or aryl, for example phenyl; $R_1$ and $R_2$ represent, independently of each other, a hydrogen atom.

Among the compounds of general formula (I) that are subjects of the invention, a third subgroup of compounds consists of the compounds for which the pyrrolopyridine nucleus is a pyrrolo[3,2-b]pyridine group, a pyrrolo[3,2-c]pyridine group, a pyrrolo[2,3-c]pyridine group or a pyrrolo[2,3-b]pyridine group;

the pyrrolopyridine nucleus being optionally substituted in the carbon position 4, 5, 6 and/or 7, for example in the carbon position 5, with one or more substituents X, which may be identical or different, for example with one substituent X, chosen from a halogen atom, for example a chlorine or fluorine atom, and a $C_1$-$C_6$-fluoroalkyl group, for example a trifluoromethyl group, or aryl, for example phenyl.

Among the compounds of general formula (I) that are subjects of the invention, a fourth subgroup of compounds consists of compounds for which the pyrrolopyridine nucleus is a pyrrolo[3,2-b]pyridine group, a pyrrolo[3,2-c]pyridine group or a pyrrolo[2,3-b]pyridine group;

the pyrrolopyridine nucleus being optionally substituted in the carbon position 4, 5, 6 and/or 7 with one or more substituents X which may be identical or different, chosen from a halogen atom and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_1$-$C_6$-fluoroalkoxyl, cyano, C(O)$NR_1R_2$, nitro, $NR_1R_2$, $C_1$-$C_6$-thioalkyl, —S(O)—$C_1$-$C_6$-alkyl, —S(O)$_2$—$C_1$-$C_6$-alkyl, $SO_2NR_1R_2$, $NR_3COR_4$, $NR_3SO_2R_5$ or aryl group, the aryl being optionally substituted with one or more substituents chosen from a halogen and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_1$-$C_6$-fluoroalkoxyl, nitro or cyano group;

$R_1$ and $R_2$ represent, independently of each other, a hydrogen atom or a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene or aryl group; or $R_1$ and $R_2$ together forming, with the nitrogen atom that bears them, an azetidine, pyrrolidine, piperidine, azepine, morpholine, thiomorpholine, piperazine or homopiperazine group, this group being optionally substituted with a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene or aryl group;

$R_3$ and $R_4$ represent, independently of each other, a hydrogen atom or a $C_1$-$C_6$-alkyl, aryl-$C_1$-$C_6$-alkylene or aryl group;

$R_5$ represents a $C_1$-$C_6$-alkyl or aryl group.

Among the compounds of general formula (I) that are subjects of the invention, a fifth subgroup of compounds consists of compounds for which $Z_1$, $Z_2$, $Z_3$, $Z_4$ and $Z_5$ represent, independently of each other, a hydrogen or halogen atom, for example a fluorine atom.

Among the compounds of general formula (I) that are subjects of the invention, a sixth subgroup of compounds consists of the compounds for which W is chosen from indolinyl, indolyl, isoindolyl, isoindolinyl, benzofuranyl, dihydrobenzofuranyl, benzothiophenyl, dihydrobenzothiophenyl, benzoxazolyl, dihydrobenzoxazolinyl, isobenzofuranyl, dihydroisobenzofuranyl, benzimidazolyl, dihydrobenzimidazolyl, indazolyl, benzothiazolyl, isobenzothiazolyl, dihydroisobenzothiazolyl, benzotriazolyl, quinolyl, dihydroquinolyl, tetrahydroquinolyl, isoquinolyl, dihydroisoquinolyl, tetrahydroisoquinolyl, benzoxazinyl, dihydrobenzoxazinyl, benzothiazinyl, dihydrobenzothiazinyl, cinnolinyl, quinazolinyl, dihydroquinazolinyl, tetrahydroquinazolinyl, quinoxalinyl, dihydroquinoxalinyl, tetrahydroquinoxalinyl, phthalazinyl, dihydrophthalazinyl, tetrahydrophthalazinyl, tetrahydrobenz[b]azepinyl, tetrahydrobenz[c]azepinyl, tetrahydrobenz[d]azepinyl, tetrahydrobenzo[b][1,4]diazepinyl, tetrahydrobenzo[e][1,4]diazepinyl, tetrahydrobenzo[b][1,4]oxazepinyl or tetrahydrobenzo[b][1,4]thiazepinyl groups; the carbon and/or nitrogen atom(s) of said group W being optionally substituted as defined in the general formula (I).

Among the compounds of general formula (I) that are subjects of the invention, a seventh subgroup of compounds consists of the compounds for which W represents a fused bicyclic group of formula:

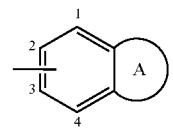

bonded to the nitrogen atom via positions 1, 2, 3 or 4;

A represents a 5- to 7-membered heterocycle comprising from one to three heteroatoms chosen from O, S and N;

and W is chosen from indolyl, benzimidazolyl, tetrahydroquinolyl, quinolyl and benzothiazolyl groups; and/or the carbon atom(s) of A being optionally substituted with one or more groups chosen from a hydrogen atom and a $C_1$-$C_6$-alkyl, for example methyl, or an oxo group; and/or the nitrogen atom(s) of A being optionally substituted with $R_6$ when the nitrogen is adjacent to a carbon atom substituted with an oxo group, or with $R_7$ in the other cases;

$R_6$ represents a hydrogen atom;

$R_7$ represents a hydrogen atom or a $C_1$-$C_6$-alkyl group, for example methyl.

The compounds for which n, X, $Z_1$, $Z_2$, $Z_3$, $Z_4$, $Z_5$ and W are all as defined in the subgroups of compounds of general formula (I) above form an eighth subgroup.

Among the compounds of general formula (I) that are subjects of the invention, a ninth subgroup of compounds consists of the compounds for which:

n is equal to 0, 1, 2 or 3;

the pyrrolopyridine nucleus is a pyrrolo[3,2-b]pyridine group, a pyrrolo[3,2-c]pyridine group, a pyrrolo[2,3-c]pyridine group or a pyrrolo[2,3-b]pyridine group;

the pyrrolopyridine nucleus being optionally substituted in the carbon position 4, 5, 6 and/or 7 with one or more substituents X, which may be identical or different, chosen from a halogen atom and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_1$-$C_6$-fluoroalkoxyl, cyano, C(O)NR$^1$R$_2$, nitro, NR$_1$R$_2$, $C_1$-$C_6$-thioalkyl, —S(O)—$C_1$-$C_6$-alkyl, —S(O)$_2$—$C_1$-$C_6$-alkyl, SO$_2$NR$_1$R$_2$, NR$_3$COR$_4$, NR$_3$SO$_2$R$_5$ or aryl group, the aryl being optionally substituted with one or more substituents chosen from a halogen and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_1$-$C_6$-fluoroalkoxyl, nitro or cyano group;

$Z_1$, $Z_2$, $Z_3$, $Z_4$ and $Z_5$ represent, independently of each other, a hydrogen or halogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_1$-$C_6$-fluoroalkoxyl, cyano, C(O)NR$_1$R$_2$, nitro, NR$_1$R$_2$, $C_1$-$C_6$-thioalkyl, —S(O)—$C_1$-$C_6$-alkyl, —S(O)$_2$—$C_1$-$C_6$-alkyl, SO$_2$NR$_1$R$_2$, NR$_3$COR$_4$, NR$_3$SO$_2$R$_5$, aryl-$C_1$-$C_6$-alkylene or aryl group, the aryl and the aryl-$C_1$-$C_6$-alkylene being optionally substituted with one or more substituents chosen from a halogen and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_1$-$C_6$-fluoroalkoxyl, nitro or cyano group;

$R_1$ and $R_2$ represent, independently of each other, a hydrogen atom or a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene or aryl group; or $R_1$ and $R_2$ together forming, with the nitrogen atom that bears them, an azetidine, pyrrolidine, piperidine, azepine, morpholine, thiomorpholine, piperazine or homopiperazine group, this group being optionally substituted with a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene or aryl group;

$R_3$ and $R_4$ represent, independently of each other, a hydrogen atom or a $C_1$-$C_6$-alkyl or aryl group;

$R_5$ represents a $C_1$-$C_6$-alkyl, aryl-$C_1$-$C_6$-alkylene or aryl group;

W represents a fused bicyclic group of formula:

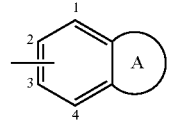

bonded to the nitrogen atom via positions 1, 2, 3 or 4;

A represents a 5- to 7-membered heterocycle comprising from one to three heteroatoms chosen from O, S and N;

the carbon atom(s) of A being optionally substituted with one or more groups chosen from a hydrogen atom and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl, aryl-$C_1$-$C_6$-alkylene, oxo or thio group;

the nitrogen atom(s) of A being optionally substituted with $R_6$ when the nitrogen is adjacent to a carbon atom substituted with an oxo group, or with $R_7$ in the other cases;

$R_6$ represents a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-$C_1$-$C_6$-alkylene or aryl group;

$R_7$ represents a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-$C_1$-$C_6$-alkylene, $C_1$-$C_6$-alkyl-C(O)—, $C_3$-$C_7$-cycloalkyl-$C_1$-$C_3$-alkylene-(CO)—, $C_1$-$C_6$-fluoroalkyl-C(O)—, $C_3$-$C_7$-cycloalkyl-C(O)—, aryl-C(O)—, aryl-$C_1$-$C_6$-alkylene-C(O)—, $C_1$-$C_6$-alkyl-S(O)$_2$—, $C_1$-$C_6$-fluoroalkyl-S(O)$_2$—, $C_3$-$C_7$-cycloalkyl-S(O)$_2$—, $C_3$-$C_7$-cycloalkyl-$C_1$-$C_3$-alkylene-S(O)$_2$—, aryl-S(O)$_2$— or aryl-$C_1$-$C_6$-alkylene-S(O)$_2$— or aryl group, with the condition that when $Z_1$, $Z_2$, $Z_3$, Z and $Z_5$ simultaneously represent hydrogen atoms and when the pyrrolopyridine nucleus is an optionally substituted pyrrolo[3,2-b]pyridine, then n is equal to 2 or 3.

Among the compounds of general formula (I) that are subjects of the invention, mention may be made of the following compounds:

N-(1-methyl-1H-indol-5-yl)-1-[(3-fluorophenyl)methyl]-1H-pyrrolo[2,3-c]pyridine-2-carboxamide;

N-(1-methyl-1H-benzimidazol-5-yl)-5-fluoro-1-[(3-fluorophenyl)methyl]-1H-pyrrolo[2,3-c]pyridine-2-carboxamide;

N-(1,2-dimethyl-1H-benzimidazol-5-yl)-5-chloro-1-[(3-fluorophenyl)methyl]-1H-pyrrolo[2,3-c]pyridine-2-carboxamide;

N-(1,2-dimethyl-1H-benzimidazol-5-yl)-1-[(3-fluorophenyl)methyl]-1H-pyrrolo[2,3-c]pyridine-2-carboxamide;

N-(2-methyl-1H-benzothiazol-5-yl)-5-fluoro-1-[(3-fluorophenyl)methyl]-1H-pyrrolo[2,3-c]pyridine-2-carboxamide;

N-(1,2-dimethyl-1H-benzimidazol-5-yl)-5-fluoro-1-[(3-fluorophenyl)methyl]-1H-pyrrolo[2,3-c]pyridine-2-carboxamide;

N-(1,2-dimethyl-1H-benzimidazol-5-yl)-5-phenyl-1-[(3-fluorophenyl)methyl]-1H-pyrrolo[2,3-c]pyridine-2-carboxamide;

N-(1-methyl-1H-indol-5-yl)-1-[(3-fluorophenyl)methyl]-1H-pyrrolo[2,3-b]pyridine-2-carboxamide;

N-(1-methyl-1H-benzimidazol-5-yl)-1-[(3-fluorophenyl)methyl]-1H-pyrrolo[2,3-b]pyridine-2-carboxamide;

N-(2-oxo-1,2,3,4-tetrahydroquinol-7-yl)-1-[(3-fluorophenyl)methyl]-1H-pyrrolo[2,3-b]pyridine-2-carboxamide;

N-(quinol-7-yl)-1-[(3-fluorophenyl)methyl]-1H-pyrrolo[2,3-b]pyridine-2-carboxamide;

N-(1-methyl-1H-indol-5-yl)-1-(phenylmethyl)-1H-pyrrolo[2,3-b]pyridine-2-carboxamide;

N-(1-methyl-1H-indol-5-yl)-1-(phenylethyl)-1H-pyrrolo[2,3-b]pyridine-2-carboxamide;

N-(2-methyl-benzothiazol-5-yl)-1-[(3-fluorophenyl)methyl]-1H-pyrrolo[2,3-b]pyridine-2-carboxamide;

N-(1-methyl-1H-benzimidazol-5-yl)-5-fluoro-1-[(3-fluorophenyl)methyl]-1H-pyrrolo[2,3-b]pyridine-2-carboxamide;

N-(1,2-dimethyl-1H-benzimidazol-5-yl)-5-trifluoromethyl-1-[(3-fluorophenyl)methyl]-1H-pyrrolo[2,3-b]pyridine-2-carboxamide;

N-(1-methyl-1H-indol-5-yl)-5-trifluoromethyl-1-[(3-fluorophenyl)methyl]-1H-pyrrolo[2,3-b]pyridine-2-carboxamide;

N-(2-methyl-benzothiazol-5-yl)-5-trifluoromethyl-1-[(3-fluorophenyl)methyl]-1H-pyrrolo[2,3-b]pyridine-2-carboxamide;

N-(1,2-dimethyl-1H-benzimidazol-5-yl)-1-[(3-fluorophenyl)methyl]-1H-pyrrolo[2,3-b]pyridine-2-carboxamide;

N-(1,2-dimethyl-1H-benzimidazol-5-yl)-5-fluoro-1-[(3-fluorophenyl)methyl]-1H-pyrrolo[2,3-b]pyridine-2-carboxamide;

N-(1,2-dimethyl-1H-benzimidazol-5-yl)-1-[(3-fluorophenyl)methyl]-1H-pyrrolo[3,2-c]pyridine-2-carboxamide;

N-(1-methyl-1H-benzimidazol-5-yl)-1-[(3-fluorophenyl)methyl]-1H-pyrrolo[3,2-b]pyridine-2-carboxamide;

N-(1,2-dimethyl-1H-benzimidazol-5-yl)-5-trifluoromethyl-1-[(3-fluorophenyl)methyl]-1H-pyrrolo[3,2-b]pyridine-2-carboxamide;

N-(2-methyl-benzothiazol-5-yl)-1-[(3-fluorophenyl)methyl]-1H-pyrrolo[3,2-b]pyridine-2-carboxamide;

N-(1,2-dimethyl-1H-benzimidazol-5-yl)-1-[(3-fluorophenyl)methyl]-1H-pyrrolo[3,2-b]pyridine-2-carboxamide;

N-(1,2-dimethyl-1H-benzimidazol-5-yl)-1-(phenyl)-1H-pyrrolo[2,3-b]pyridine-2-carboxamide.

Among the compounds of general formula (I) that are subjects of the invention, a subgroup of compounds consists of the compounds of general formula (I')

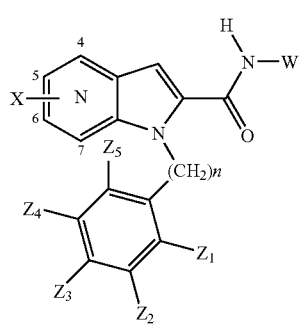

(I')

in which n is equal to 1, 2 or 3;

the pyrrolopyridine nucleus is a pyrrolo[3,2-b]pyridine group, a pyrrolo[3,2-c]pyridine group, a pyrrolo[2,3-c]pyridine group or a pyrrolo[2,3-b]pyridine group;

the pyrrolopyridine nucleus being optionally substituted in the carbon position 4, 5, 6 and/or 7 with one or more substituents X, which may be identical or different, chosen from a halogen atom and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_1$-$C_6$-fluoroalkoxyl, cyano, C(O)NR$_1$R$_2$, nitro, NR$_1$R$_2$, $C_1$-$C_6$-thioalkyl, —S(O)—$C_1$-$C_6$-alkyl, —S(O)$_2$—$C_1$-$C_6$-alkyl, SO$_2$NR$_1$R$_2$, NR$_3$COR$_4$, NR$_3$SO$_2$R$_5$ or aryl group, the aryl being optionally substituted with one or more substituents chosen from a halogen and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_1$-$C_6$-fluoroalkoxyl, nitro or cyano group;

$Z_1$, $Z_2$, $Z_3$, $Z_4$ and $Z_5$ represent, independently of each other, a hydrogen or halogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_1$-$C_6$-fluoroalkoxyl, cyano, C(O)NR$_1$R$_2$, nitro, NR$_1$R$_2$, $C_1$-$C_6$-thioalkyl, —S(O)—$C_1$-$C_6$-alkyl, —S(O)$_2$—$C_1$-$C_6$-alkyl, SO$_2$NR$_1$R$_2$, NR$_3$COR$_4$, NR$_3$SO$_2$R$_5$, aryl-$C_1$-$C_6$-alkylene or aryl group, the aryl and the aryl-$C_1$-$C_6$-alkylene being optionally substituted with one or more substituents chosen from a halogen and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_1$-$C_6$-fluoroalkoxyl, nitro or cyano group;

$R_1$ and $R_2$ represent, independently of each other, a hydrogen atom or a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene or aryl group; or $R_1$ and $R_2$ together forming, with the nitrogen atom that bears them, an azetidine, pyrrolidine, piperidine, azepine, morpholine, thiomorpholine, piperazine or homopiperazine group, this group being optionally substituted with a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene or aryl group;

$R_3$ and $R_4$ represent, independently of each other, a hydrogen atom or a $C_1$-$C_6$-alkyl, aryl-$C_1$-$C_6$-alkylene or aryl group;

$R_5$ represents a $C_1$-$C_6$-alkyl or aryl group;

W represents a fused bicyclic group of formula:

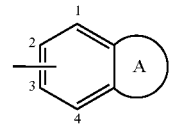

bonded to the nitrogen atom via positions 1, 2, 3 or 4;

A represents a 5- to 7-membered heterocycle comprising from one to three heteroatoms chosen from O, S and N;

the carbon atom(s) of A being optionally substituted with one or more groups chosen from a hydrogen atom and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl, aryl-$C_1$-$C_6$-alkylene, oxo or thio group;

the nitrogen atom(s) of A being optionally substituted with $R_6$ when the nitrogen is adjacent to a carbon atom substituted with an oxo group, or with $R_7$ in the other cases;

$R_6$ represents a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-$C_1$-$C_6$-alkylene or aryl group;

$R_7$ represents a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-$C_1$-$C_6$-alkylene, $C_1$-$C_6$-alkyl-C(O)—, $C_3$-$C_7$-cycloalkyl-$C_1$-$C_3$-alkylene-(CO)—, $C_1$-$C_6$-fluoroalkyl-C(O)—, $C_3$-$C_7$-cycloalkyl-C(O)—, aryl-C(O)—, aryl-$C_1$-$C_6$-alkylene-C(O)—, $C_1$-$C_6$-alkyl-S(O)$_2$—, $C_1$-$C_6$-fluoroalkyl-S(O)$_2$—, $C_3$-$C_7$-cycloalkyl-S(O)$_2$—, $C_3$-$C_7$-cycloalkyl-$C_1$-$C_3$-alkylene-S(O)$_2$—, aryl-S(O)$_2$— or aryl-$C_1$-$C_6$-alkylene-S(O)$_2$— or aryl group.

Among the compounds of general formula (I') that are subjects of the invention, a first subgroup of compounds consists of the compounds for which n is equal to 1 or 2.

Among the compounds of general formula (I') that are subjects of the invention, a second subgroup of compounds consists of the compounds for which the pyrrolopyridine nucleus is a pyrrolo[2,3-c]pyridine group or a pyrrolo[2,3-b]pyridine group optionally substituted in the carbon position 4, 5, 6 and/or 7 with one or more substituents X, which may be identical or different, chosen from a hydrogen or halogen atom, for example a fluorine, a bromine or a chlorine, or a $C_1$-$C_6$-alkyl group, for example a methyl, a propyl, an isopropyl, a sec-butyl, a tert-butyl or a pentyl, $C_3$-$C_7$-cycloalkyl, for example a cyclopentyl or a cyclohexyl, $C_1$-$C_6$-fluoroalkyl, for example a trifluoromethyl group, $C_1$-$C_6$-alkoxyl, for example a methoxy or an ethoxy, $C_1$-$C_6$-fluoroalkoxyl, for example a trifluoromethoxy group, nitro, $NR_1R_2$, $C_1$-$C_6$-thioalkyl, for example a thiomethyl, —S(O)—$C_1$-$C_6$-alkyl, —S(O)$_2$—$C_1$-$C_6$-alkyl, for example an —S(O)$_2$—$CH_3$, or aryl, for example phenyl; $R_1$ and $R_2$ represent, independently of each other, a hydrogen atom.

Among the compounds of general formula (I') that are subjects of the invention, a third subgroup of compounds consists of the compounds for which the pyrrolopyridine nucleus is a pyrrolo[2,3-c]pyridine group or a pyrrolo[2,3-b]pyridine group optionally substituted in the carbon position 4, 5, 6 and/or 7, for example in the carbon position 5, with one or more substituents X, which may be identical or different, for example with one substituent X, chosen from a halogen atom, for example a chlorine or fluorine atom, or a $C_1$-$C_6$-fluoroalkyl group, for example a trifluoromethyl group.

Among the compounds of general formula (I') that are subjects of the invention, a fourth subgroup of compounds consists of the compounds for which $Z_1$, $Z_2$, $Z_3$, $Z_4$ and $Z_5$ represent, independently of each other, a hydrogen or halogen atom, for example a fluorine atom.

Among the compounds of general formula (I') that are subjects of the invention, a fifth subgroup of compounds consists of the compounds for which W is chosen from indolinyl, indolyl, isoindolyl, isoindolinyl, benzofuranyl, dihydrobenzofuranyl, benzothiophenyl, dihydrobenzothiophenyl, benzoxazolyl, dihydrobenzoxazolinyl, isobenzofuranyl, dihydroisobenzofuranyl, benzimidazolyl, dihydrobenzimidazolyl, indazolyl, benzothiazolyl, isobenzothiazolyl, dihydroisobenzothiazolyl, benzotriazolyl, quinolyl, dihydroquinolyl, tetrahydroquinolyl, isoquinolyl, dihydroisoquinolyl, tetrahydroisoquinolyl, benzoxazinyl, dihydrobenzoxazinyl, benzothiazinyl, dihydrobenzothiazinyl, cinnolinyl, quinazolinyl, dihydroquinazolinyl, tetrahydroquinazolinyl, quinoxalinyl, dihydroquinoxalinyl, tetrahydroquinoxalinyl, phthalazinyl, dihydrophthalazinyl, tetrahydrophthalazinyl, tetrahydrobenz[b]azepinyl, tetrahydrobenz[c]azepinyl, tetrahydrobenz[d]azepinyl, tetrahydrobenzo[b][1,4]diazepinyl, tetrahydrobenzo[e][1,4]diazepinyl, tetrahydro-benzo[b][1,4]oxazepinyl or tetrahydrobenzo[b][1,4]thiazepinyl;

the carbon and/or nitrogen atom(s) of the said group W being optionally substituted as defined in the general formula (I).

Among the compounds of general formula (I') that are subjects of the invention, a sixth subgroup of compounds consists of the compounds for which W represents a fused bicyclic group of formula:

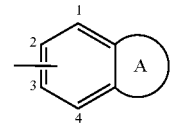

bonded to the nitrogen atom via positions 1, 2, 3 or 4;

A represents a 5- to 7-membered heterocycle comprising from one to three heteroatoms chosen from O, S or N;

and W is chosen from indolyl, benzimidazolyl, dihydroquinolyl, quinolyl and benzothiazolyl groups; and/or the carbon atom(s) of A being optionally substituted with one or more groups chosen from a hydrogen atom and a $C_1$-$C_6$-alkyl group, for example methyl; and/or the nitrogen atom(s) of A being optionally substituted with $R_7$;

$R_7$ represents a hydrogen atom or a $C_1$-$C_6$-alkyl group, for example methyl.

The compounds for which n, X, $Z_1$, $Z_2$, $Z_3$, $Z_4$, $Z_5$ and W are all as defined in the subgroups of compounds of general formula (I') above form a seventh subgroup.

In the context of the present invention, the following meanings apply:

$C_t$-$C_z$ in which t and z may take the values from 1 to 7: a carbon-based chain possibly containing from t to z carbon atoms, for example $C_1$-$C_3$ is a carbon-based chain that may contain from 1 to 3 carbon atoms;

an alkyl: a saturated, linear or branched aliphatic group. Examples that may be mentioned include methyl, ethyl, propyl, isopropyl, butyl, isobutyl, tert-butyl, pentyl, etc. groups;

an alkylene: a saturated, linear or branched divalent alkyl group, for example a $C_{1-3}$-alkylene group represents a linear or branched divalent carbon-based chain of 1 to 3 carbon atoms, for example a methylene, ethylene, 1-methylethylene or propylene;

a cycloalkyl: a cyclic carbon-based group. Examples that may be mentioned include cyclopropyl, cyclobutyl, cyclopentyl, cyclohexyl, etc. groups;

a fluoroalkyl: an alkyl group of which one or more hydrogen atoms have been substituted with a fluorine atom;

an alkoxy: a radical —O-alkyl in which the alkyl group is as defined above;

a fluoroalkoxy: an alkoxy group of which one or more hydrogen atoms have been substituted with a fluorine atom;

a thioalkyl: a radical —S-alkyl in which the alkyl group is as defined above;

an aryl: a cyclic aromatic group containing between 6 and 10 carbon atoms. Examples of aryl groups that may be mentioned include phenyl and naphthyl groups;

a heterocycle: a saturated, partially unsaturated or aromatic 5- to 7-membered cyclic group comprising from one to three heteroatoms chosen from O, S and N;

a halogen atom: a fluorine, a chlorine, a bromine or an iodine;

"oxo" means "═O";

"thio" means "═S".

The compounds of formula (I) may comprise one or more asymmetric carbon atoms. They may thus exist in the form of enantiomers or diastereoisomers. These enantiomers and diastereoisomers, and also mixtures thereof, including racemic mixtures, form part of the invention.

The compounds of formula (I) may exist in the form of bases or of acid-addition salts. Such addition salts form part of the invention.

These salts are advantageously prepared with pharmaceutically acceptable acids, but the salts of other acids that are useful, for example, for purifying or isolating the compounds of formula (I) also form part of the invention.

The compounds of general formula (I) may be in the form of hydrates or solvates, i.e. in the form of associations or combinations with one or more water molecules or with a solvent. Such hydrates and solvates also form part of the invention.

In the text hereinbelow, the term "leaving group" means a group that can be readily cleaved from a molecule by breaking a heterolytic bond, with loss of an electron pair. This group may thus be readily replaced with another group, for example during a substitution reaction. Such leaving groups are, for example, halogens or an activated hydroxyl group such as a methanesulfonate, benzenesulfonate, p-toluenesulfonate, triflate, acetate, etc. Examples of leaving groups and references for preparing them are given in "Advances in Organic Chemistry", J. March, $5^{th}$ Edition, Wiley Interscience, 2001.

In accordance with the invention, the compounds of general formula (I) may be prepared according to the process illustrated in scheme 1 below.

According to scheme 1, the compounds of general formula (IV) may be obtained by reacting a compound of general formula (II) in which X is as defined in the general formula (I) above and B represents a $C_1$-$C_6$-alkoxyl or hydroxyl group, with a compound of general formula (III), in which $Z_1$, $Z_2$, $Z_3$, $Z_4$, $Z_5$ and n are as defined in the general formula (I) above and R' represents a leaving group or a hydroxyl group when n is equal to 1, 2 or 3 or R' represents a leaving group when n is equal to 0.

When the compound of general formula (III) is defined such that n is equal to 1, 2 or 3 and R' represents a leaving group such as a bromine or iodine atom, the reaction may be performed in the presence of a base such as sodium hydride or potassium carbonate, in a polar solvent such as dimethylformamide, dimethyl sulfoxide or acetone (n=1: Kolasa T., Bioorg. Med. Chem. 1997, 5 (3) 507, n=2: Abramovitch R., Synth. Commun., 1995, 25(1), 1).

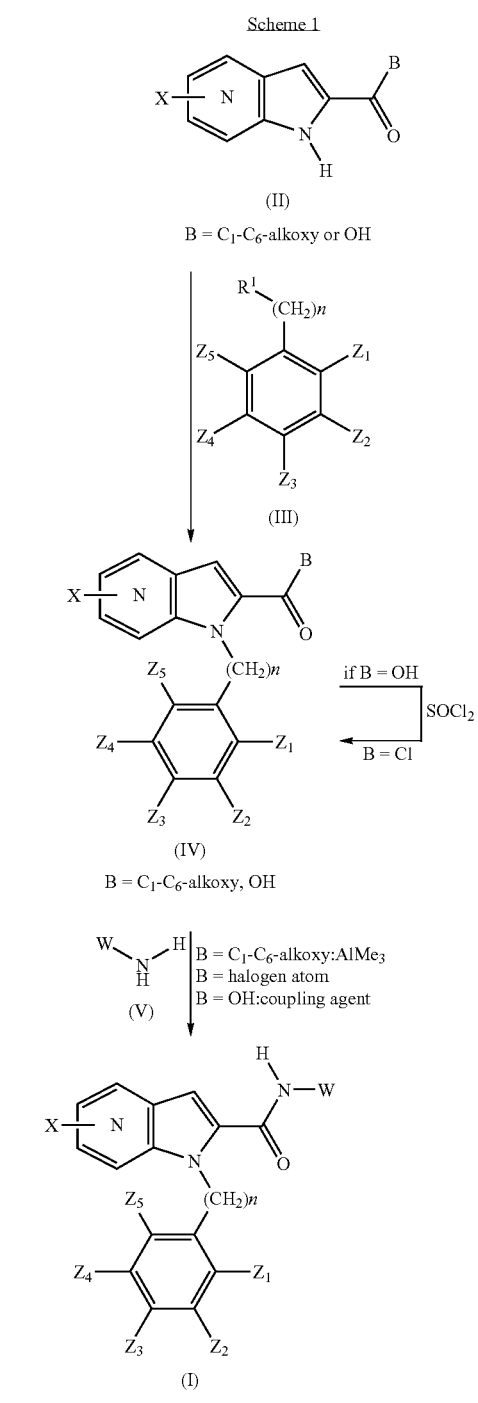

When the compound of general formula (III) is defined such that n is equal to 1, 2 or 3 and R' represents a hydroxyl group, the compounds of general formula (IV) may be obtained by reacting the compound of general formula (II) with a compound of general formula (III) in the presence of a phosphine such as triphenylphosphine and a reagent such as diethyl azodicarboxylate in solution in a solvent such as dichloromethane or tetrahydrofuran (O. Mitsunobu, Synthesis, 1981, 1-28).

When the compound of general formula (III) is defined such that n is equal to 0, R' represents a leaving group such as a chlorine, bromine or iodine atom and the reaction may be performed at a temperature of between 80° C. and 250° C., in the presence of a copper-based catalyst such as copper bromide or copper oxide and also of a base such as potassium carbonate (Murakami Y., *Chem. Pharm. Bull.*, 1995, 43 (8), 1281). The milder conditions described in S. L. Buchwald, *J. Am. Chem. Soc.* 2002, 124, 11684 may also be used.

In the context of the invention, the compounds of general formula (IV) in which B represents a $C_1$-$C_6$-alkoxyl group may be converted into compounds of general formula (IV) in which B represents a hydroxyl group according to methods known to those skilled in the art, for example in the presence of a base such as sodium hydroxide in a solvent such as methanol or ethanol.

In the context of the invention, the compounds of general formula (IV) in which B represents a hydroxyl group may be converted into compounds of general formula (IV) in which B represents a $C_1$-$C_6$-alkoxyl group according to methods known to those skilled in the art, for example in the presence of an acid such as sulfuric acid in a solvent such as methanol or ethanol.

In the case of the compounds of general formula (IV), in which B represents a $C_1$-$C_6$-alkoxyl group, the compound of general formula (I) can be obtained by reacting a compound of general formula (IV), as obtained above, with an amide of the compound of general formula (V), in which W is as defined in general formula (I) above, at the reflux point of a solvent such as toluene. The aluminum amide of the compound of general formula (V) is prepared by first reacting trimethylaluminum with the amines of general formula (V).

In the case of the compounds of general formula (IV), in which B represents a hydroxyl group, the carboxylic acid function may be converted beforehand into an acid halide such as an acid chloride via the action of thionyl chloride, at the reflux point of a solvent such as dichloromethane or dichloroethane. The compound of general formula (I) is then obtained by reacting the compound of general formula (IV), in which B represents a chlorine atom, with the compound of general formula (V), in the presence of a base such as triethylamine or sodium carbonate.

Alternatively, the compounds of general formula (IV), in which B represents a hydroxyl group, may be coupled with the compounds of general formula (V) in the presence of a coupling agent such as a dialkyl carbodiimide, benzotriazol-1-yloxytris(pyrrolidinophosphonium) hexafluorophosphate, diethyl cyanophosphonate or any other coupling agent known to those skilled in the art, in the presence of a base such as triethylamine, in a solvent such as dimethylformamide.

In scheme 1, the compounds of formula (II), (III) and (V) and the other reagents, when their preparation method is not described, are commercially available, described in the literature or prepared by analogy with numerous processes described in the literature (M. Nazare et al *Angew Chem Int Ed* 2004, 43(34), 4526-4528; P. M. Fresneda et al *Tetrahedron Lett* 2000, 41(24), 4777-4780; M. H. Fisher et al *J Heterocyclic Chem* 1969, 6, 775; B. Frydman et al *J Am Chem Soc* 1965, 87, 3530; L. N. Yakhontov *Tetrahedron Lett* 1969, 1909; G. P. Fagan et al *J Med Chem* 1988 31(5), 944; OSI Pharmaceuticals WO2004104001; WO03049702; U.S. Pat. No. 0,149,367; WO03068749, US20050131012, for example).

The compounds of general formula (II), (IV) or (I), in which X represents an alkyl group, may be obtained via a coupling reaction, catalyzed with a metal such as palladium or iron, performed on the corresponding compounds of general formula (II), (IV) or (I), in which X represents a halogen atom, for example a chlorine, for example in the presence of an alkylmagnesium halide or an alkylzinc halide according to methods described in the literature (A. Furstner et al *J Am Chem Soc* 2002, 124(46), 13856; G. Quéguiner et al *J Org Chem* 1998, 63(9), 2892 for example) or known to those skilled in the art.

The compounds of general formulae (II), (IV) and (I), in which X, $Z_1$, $Z_2$, $Z_3$, $Z_4$ and/or $Z_5$ represent a cyano group or an aryl, may be obtained via a coupling reaction, catalyzed with a metal such as palladium, performed on the corresponding compounds of general formula (II), (IV) or (I), in which X, $Z_1$, $Z_2$, $Z_3$, $Z_4$ and/or $Z_5$ represents, for example, a bromine atom, in the presence of trimethylsilyl cyanide or an arylboronic acid, or via any other methods described in the literature or known to those skilled in the art.

The compounds of general formulae (I), (II) and (IV), in which X, $Z_1$, $Z_2$, $Z_3$, $Z_4$ and/or $Z_5$ represent a group $NR_1R_2$, $NR_3COR_4$ or $NR_3SO_2R_5$, may be obtained from the corresponding compounds of general formulae (I), (II) and (IV), in which X, $Z_1$, $Z_2$, $Z_3$, $Z_4$ and/or $Z_5$ represents, for example, a bromine atom, via a coupling reaction with, respectively, an amine, an amide or a sulfonamide in the presence of a base, a phosphine and a palladium-based catalyst, according to methods described in the literature or known to those skilled in the art.

The compounds of general formulae (II), (IV) and (I), in which X, $Z_1$, $Z_2$, $Z_3$, $Z_4$ and/or $Z_5$ represent a group $C(O)NR_1R_2$, may be obtained from the corresponding compounds of general formula (II), (IV) or (I), in which X, $Z_1$, $Z_2$, $Z_3$, $Z_4$ and/or $Z_5$ represents a cyano group, according to methods described in the literature or known to those skilled in the art.

The compounds of general formulae (II), (IV) and (I), in which X, $Z_1$, $Z_2$, $Z_3$, $Z_4$ and/or $Z_5$ represent a group —S(O)-alkyl or —S(O)$_2$-alkyl, may be obtained by oxidation of the corresponding compounds of general formula (II), (IV) or (I), in which X, $Z_1$, $Z_2$, $Z_3$, $Z_4$ and/or $Z_5$ represents a $C_1$-$C_6$-thioalkyl group, according to methods described in the literature or known to those skilled in the art.

The compounds of general formulae (II), (IV) and (I), in which X, $Z_1$, $Z_2$, $Z_3$, $Z_4$ and/or $Z_5$ represent a group $NR_1R_2$, $NR_3COR_4$ or $NR_3SO_2R_5$, may be obtained from the corresponding compounds of general formula (II), (IV) or (I), in which X, $Z_1$, $Z_2$, $Z_3$, $Z_4$ and/or $Z_5$ represents a nitro group, for example by reduction, followed by acylation or sulfonylation, according to methods described in the literature or known to those skilled in the art.

The compounds of general formulae (II), (IV) and (I), in which X, $Z_1$, $Z_2$, $Z_3$, $Z_4$ and/or $Z_5$ represent a group $SO_2NR_1R_2$, may be obtained via a method analogous to that described in *Pharmazie* 1990, 45, 346, or according to methods that are described in the literature or that are known to those skilled in the art.

The compounds of general formula (I) in which $R_7$ represents a hydrogen atom may be obtained from compounds of general formula (I) in which, for example, $R_7$ represents a phenylmethyl group, by hydrogenation in the presence of a palladium-based catalyst, or by any method described in the literature or known to those skilled in the art.

The examples that follow describe the preparation of certain compounds in accordance with the invention. These examples are not limiting and serve merely to illustrate the present invention. The numbers of the compounds given as examples refer to those given in Table 1. The elemental microanalyses, the LC-MS (liquid chromatography coupled to mass spectrometry) analyses and the IR or NMR spectra confirm the structures of the compounds obtained.

EXAMPLE 1

Compound 1

N-(1-methyl-1H-indol-5-yl)-1-[(3-fluorophenyl)methyl]-1H-pyrrolo[2,3-c]pyridine-2-carboxamide 1.1 ethyl 3-(3-nitropyridin-4-yl)-2-oxopropionate 3.1 g (22.44 mmol) of 4-methyl-3-nitropyridine and 16.39 g (112.22 mmol) of ethyl oxalate are placed in a 100 ml three-necked flask equipped with a magnetic stirrer and maintained under a flush of nitrogen. 3.69 ml (24.69 mmol) of 1,8-diaza-bicyclo[5.4.0]undec-7-ene are then added to the reaction medium stirred at room temperature. The reaction mixture is then stirred at room temperature for 1 hour and then diluted with a mixture of ethyl acetate (150 ml), water (100 ml) and acetic acid (4 ml). The mixture is extracted twice with ethyl acetate. The combined organic phases are washed with 100 ml of water, with 100 ml of saturated aqueous sodium chloride solution, dried over sodium sulfate and then concentrated under reduced pressure. The crude reaction product is then triturated from pentane, filtered and then heated in petroleum ether, filtered and dried under reduced pressure. 3.9 g (16.37 mmol) of product are thus isolated, and are used without further purification in the following step.

$^1$H NMR (CDCl$_3$), δ (ppm): 9.4 (s, 1H); 8.9 (d, 1H); 7.4 (d, 1H) 4.65 (s, 2H); 4.5 (q, 2H); 1.4 (t, 3H).

1.2 ethyl 1H-pyrrolo[2,3-c]pyridine-2-carboxylate

Method A: To a solution of 3.9 g (16.37 mmol) of product obtained in step 1.1 in 140 ml of ethanol and 60 ml of tetrahydrofuran are added in a single portion 60 ml of saturated aqueous ammonium chloride solution and 5.48 g (98.2 mmol) of iron powder. The reaction mixture is then stirred at reflux for 2 hours. The cooled solution is filtered through Celite, which is rinsed several times with ethyl acetate. After concentrating the filtrate under reduced pressure, the residue is taken up in water and ethyl acetate and the organic phase is washed with saturated aqueous sodium chloride solution and then dried over sodium sulfate. A first crop of 0.7 g (3.68 mmol) of product is isolated. The aqueous phase is concentrated under reduced pressure, the residue is taken up in hot ethyl acetate, the precipitate is removed by filtration and the filtrate is concentrated again. The residue obtained is purified by chromatography on a column of silica gel eluting with a mixture of heptane and ethyl acetate. A further 0.7 g (3.68 mmol) of product is obtained.

Method B: To a solution of 0.25 g (1.05 mmol) of product obtained in step 1.1 in 10 ml of ethanol is added 0.11 g (0.1 mmol) of 10% palladium-on-charcoal. The reaction mixture is hydrogenated under a pressure of 30 psi for 2 hours 30 minutes at room temperature. After filtering through glass fiber, the filtrate is evaporated under reduced pressure and the crude reaction product obtained is recrystallized from ethanol to give 0.08 g (0.42 mmol) of product.

$^1$H NMR (DMSO D$_6$), δ (ppm): 8.9 (s, 1H); 8.3 (d, 1H); 7.7 (dd, 1H); 7.2 (d, 1H); 4.4 (q, 2H); 1.4 (t, 3H).

1.3 ethyl 1-[(3-fluorophenyl)methyl]-1H-pyrrolo[2,3-c]pyridine-2-carboxylate

To a solution of 2 g (10.52 mmol) of product obtained in step 1.2 in 105 ml of dry tetrahydrofuran, maintained under an inert atmosphere, are successively added with stirring 2.03 g (15.77 mmol) of 3-fluorobenzyl alcohol and then 4.17 g (15.77 mmol) of triphenylphosphine. 2.83 g (15.77 mmol) of diethyl azodicarboxylate are then added dropwise at 0° C. The reaction mixture is then stirred for 20 hours at room temperature, and then concentrated under reduced pressure. The resulting oil is purified by successive chromatographies on a column of silica gel eluting with a mixture of heptane and ethyl acetate. 1.9 g (6.37 mmol) of product are isolated.

$^1$H NMR (CDCl$_3$), δ (ppm): 8.8 (s, 1H); 8.3 (d, 1H); 7.6 (d, 1H); 7.2 (s, 1H); 7.1 (m, 1H); 6.85 (m, 2H); 6.65 (m, 1H); 5.8 (s, 2H); 4.3 (q, 2H); 1.3 (t, 3H).

1.4 N-(1-methyl-1H-indol-5-yl)-1-[(3-fluorophenyl)methyl]-1H-pyrrolo[2,3-c]pyridine-2-carboxamide (Compound 1)

A solution of 0.29 g (2.01 mmol) of 5-amino-1-methylindole in 10 ml of dry toluene is added, without heating, under argon and with magnetic stirring, to a solution of 1.68 ml (3.35 mmol) of trimethylaluminum in 5 ml of dry toluene. The reaction medium is maintained at 50° C. for 15 minutes. 0.5 g (1.68 mmol) of ester obtained in step 1.3 dissolved in 15 ml of toluene is then added slowly and the mixture is refluxed for 20 hours. Ice, dilute hydrochloric acid and then ethyl acetate are added to the cooled solution. The insoluble material is collected and taken up in dichloromethane and sodium hydroxide solution. The organic phase is washed with water, dried and concentrated under reduced pressure. The residue is purified by chromatography on a column of silica eluting with a mixture of dichloromethane and ethyl acetate. The solid obtained is triturated with petroleum ether, collected by filtration and dried under reduced pressure. 0.385 g of expected product is isolated.

Melting point: 213-214.5° C.

$^1$H NMR (DMSO D$_6$), δ (ppm): 10.45 (s, 1H); 8.95 (s, 1H); 8.2 (d, 1H); 7.95 (s, 1H); 7.7 (d, 1H); 7.3 (m, 5H); 7.0 (m, 3H); 6.4 (d, 1H); 5.95 (s, 2H); 3.75 (s, 3H).

EXAMPLE 2

Compound 2

N-(1-methyl-1H-benzimidazol-5-yl)-5-fluoro-1-[(3-fluorophenyl)methyl]-1H-pyrrolo[2,3-c]pyridine-2-carboxamide 2.1 ethyl 3-(2-fluoro-5-nitro-4-pyridyl)-2-oxopropionate 2 g (12.81 mmol) of 2-fluoro-4-methyl-5-nitropyridine and 9.36 g (32.03 mmol) of ethyl oxalate are placed in a 100 ml three-necked flask equipped with a magnetic stirrer and maintained under a flush of nitrogen. 2.11 ml (14.09 mmol) of 1,8-diazabicyclo-[5.4.0]undec-7-ene are then added to the reaction medium stirred at room temperature. The reaction mixture is then stirred at room temperature for 4 hours. A mixture of ethyl acetate (100 ml), water (40 ml) and acetic acid (2 ml) is then added. The mixture is extracted twice with ethyl acetate. The combined organic phases are washed with 100 ml of water and with 100 ml of saturated aqueous sodium chloride solution, dried over sodium sulfate and then concentrated under reduced pressure. The residue is purified by chromatography on a column of silica, eluting with a mixture of heptane and ethyl acetate. 1.53 g of product are thus isolated, and are used without further purification in the following step.

$^1$H NMR (DMSO D$_6$), δ (ppm): 8.9 (s, 1H); 7.9 (s, 1H); 6.7 (s, 1H); 4.7 (s, OH); 4.3 (q, 2H); 1.3 (t, 3H); majority keto-enol form.

2.2 ethyl 5-fluoro-1H-pyrrolo[2,3-c]pyridine-2-carboxylate

To a solution of 0.6 g (2.34 mmol) of product obtained in step 2.1 in 30 ml of ethanol and 15 ml of tetrahydrofuran are added in a single portion 15 ml of saturated aqueous ammonium chloride solution and 0.39 g (7.03 mmol) of iron powder. The reaction mixture is then stirred at reflux for 3 hours. The cooled solution is filtered through Celite and the filtrate is rinsed several times with methanol. After concentrating under reduced pressure, the residue is taken up in ethyl acetate and water. The aqueous phase is extracted with ethyl acetate and the combined organic phases are washed with 100 ml of saturated aqueous sodium chloride solution and then dried over sodium sulfate, filtered and evaporated under reduced pressure. 0.43 g (2.06 mmol) of product is obtained, and is used without further purification in the following step.

$^1$H NMR (DMSO D$_6$), δ (ppm): 12.5 (s, NH); 8.5 (s, 1H); 7.3 (s, 1H); 7.1 (s, 1H); 4.4 (q, 2H); 1.35 (t, 3H).

2.3 ethyl 5-fluoro-1-[(3-fluorophenyl)methyl]-1H-pyrrolo[2,3-c]pyridine-2-carboxylate To a solution of 0.4 g (1.92 mmol) of product obtained in step 2.2 in 20 ml of dry tetrahydrofuran, maintained under an inert atmosphere, are successively added with stirring, 0.37 g (2.88 mmol) of 3-fluorobenzyl alcohol and then 0.76 g (2.88 mmol) of triphenylphosphine. 0.52 g (2.88 mmol) of diethyl azodicarboxylate is then added dropwise at 0° C. The reaction mixture is then stirred for 20 hours at room temperature, and then concentrated under reduced pressure. The resulting oil is purified by chromatography on a column of silica gel, eluting with a mixture of n-pentane and ether. 0.49 g (1.55 mmol) of product is isolated, and is used without further purification in the following step.

$^1$H NMR (DMSO D$_6$), δ (ppm): 8.7 (s, 1H); 8.5-7.1 (m, 6H); 5.9 (s, 2H); 4.3 (q, 2H); 1.25 (t, 3H).

2.4 N-(1-methyl-1H-benzimidazol-5-yl)-5-fluoro-1-[(3-fluorophenyl)methyl]-1H-pyrrolo[2,3-c]pyridine-2-carboxamide (Compound 2)

0.3 g (2.05 mmol) of 5-amino-1-methylbenzimidazole and 10 ml of dry toluene are placed, under a stream of nitrogen, in a 100 ml three-necked flask cooled to 0° C. and equipped with a magnetic stirrer. 1.58 ml (3.16 mmol) of a 2M solution of trimethylaluminum in toluene are then added slowly to this solution. The reaction mixture obtained is maintained under a nitrogen atmosphere and stirred while allowing the temperature to rise gradually to 70° C. A solution of 0.5 g (1.58 mmol) of product obtained in step 2.3 in 10 ml of dry toluene is then added dropwise over 5 minutes, via an addition funnel. The reaction mixture is then refluxed for 2 hours. 10 ml of 1N hydrochloric acid and 20 ml of ice-water are then added to the solution cooled to 0° C. After stirring for 1 hour at room temperature, the precipitate formed is collected by filtration, washed with water, dried under reduced pressure and recrystallized from isopropanol. The expected product is isolated in the form of a yellow solid.

Melting point: 279-281° C.

$^1$H NMR (DMSO D$_6$), δ (ppm): 10.6 (s, 1H); 8.65 (s, 1H); 8.15 (s, 1H); 8.05 (s, 1H); 7.65 (m, 2H); 7.35 (m, 3H); 6.99 (m, 3H); 5.9 (s, 2H); 3.9 (s, 3H).

EXAMPLE 3

Compound 3

N-(1,2-dimethyl-1H-benzimidazol-5-yl)-5-chloro-1-[(3-fluorophenyl)methyl]-1H-pyrrolo[2,3-c]pyridine-2-carboxamide

3.1 ethyl 3-(2-chloro-5-nitro-4-pyridyl)-2-oxopropionate 1 g (5.79 mmol) of 2-chloro-4-methyl-5-nitropyridine and 4.23 g (28.94 mmol) of ethyl oxalate are placed, under a stream of nitrogen, in a 100 ml three-necked flask equipped with a magnetic stirrer. 0.96 ml (6.4 mmol) of 1,8-diazabicyclo[5.4.0]undec-7-ene is then added to the reaction medium stirred at room temperature. The reaction mixture is then stirred at room temperature for 1 hour, and then diluted with a mixture of ethyl acetate (40 ml), water (30 ml) and acetic acid (1 ml). The mixture is extracted twice with ethyl acetate. The combined organic phases are washed with 100 ml of water, with 100 ml of saturated aqueous sodium chloride solution, dried over sodium sulfate and then concentrated under reduced pressure. The residue is purified by chromatography on a column of silica gel, eluting with a mixture of heptane and ethyl acetate. 1.33 g (4.87 mmol) of the expected product are thus isolated in the form of a pink powder.

3.2 ethyl 5-chloro-1H-pyrrolo[2,3-c]pyridine-2-carboxylate

To a solution of 1.5 g (5.5 mmol) of product obtained in step 3.1 in 50 ml of ethanol and 25 ml of tetrahydrofuran are added in a single portion 25 ml of saturated aqueous ammonium chloride solution and 0.92 g (16.5 mmol) of iron powder. The reaction mixture is then stirred at reflux for 3 hours. The cooled solution is filtered through Celite, the filtrate is extracted with ethyl acetate and the combined organic phases are washed with 100 ml of saturated aqueous sodium chloride solution and then dried over sodium sulfate, filtered and evaporated under reduced pressure. The product is purified by chromatography on a column of silica, eluting with a mixture of n-heptane and ethyl acetate. 0.98 g (4.36 mmol) of the expected product is obtained in the form of a white powder.

$^1$H NMR (CDCl$_3$), δ (ppm): 9.25 (s, NH); 8.75 (s, 1H); 7.70 (s, 1H); 7.2 (d, 1H); 4.5 (q, 2H); 1.4 (t, 3H).

3.3 ethyl 5-chloro-1-[(3-fluorophenyl)methyl]-1H-pyrrolo[2,3-c]pyridine-2-carboxylate To a solution of 0.25 g (1.11 mmol) of product obtained in step 3.2, in 10 ml of dry tetrahydrofuran, maintained under an inert atmosphere, are successively added with stirring 0.21 g (1.67 mmol) of 3-fluorobenzyl alcohol and then 0.44 g (1.67 mmol) of triphenylphosphine. 0.3 g (1.67 mmol) of diethyl azodicarboxylate is added dropwise at 0° C. The reaction mixture is then stirred for 20 hours at room temperature and then concentrated under reduced pressure. The resulting oil is purified by chromatography on a column of silica gel, eluting with a mixture of n-heptane and ethyl acetate (50/50). 0.32 g (0.96 mmol) of the expected product is isolated in the form of a white powder.

$^1$H NMR (DMSO D$_6$), δ (ppm): 8.9 (s, 1H); 7.9 (s, 1H); 7.3 (s, 1H); 7.25 (m, 1H); 7.1 (m, 1H); 6.9 (m, 2H); 5.9 (s, 2H); 4.3 (q, 2H); 1.3 (t, 3H).

3.4 5-chloro-1-[(3-fluorophenyl)methyl]-1H-pyrrolo[2,3-c]pyridine-2-carboxylic acid To a solution of 0.3 g (0.9 mmol) of product obtained in step 3.3, in 10 ml of ethanol, is added 0.6 ml (1.17 mmol) of 2N sodium hydroxide solution. The reaction mixture is refluxed for 2 hours and then concentrated to dryness under reduced pressure. The resulting solid is dissolved in 15 ml of water. The pH of the solution is acidified at 0° C. to pH 3 by addition of acetic acid and the mixture is stirred for 30 minutes. The precipitate formed is filtered off, rinsed several times with water and then dried under reduced pressure. 0.25 g (0.82 mmol) of the expected product is isolated in the form of a white powder.

$^1$H NMR (DMSO D$_6$), δ (ppm): 8.9 (s, 1H); 7.9 (s, 1H); 7.3 (s, 1H); 7.25 (m, 1H); 7.1 (m, 1H); 6.9 (m, 2H); 5.9 (s, 2H)

3.5 N-(1,2-dimethyl-1H-benzimidazol-5-yl)-5-chloro-1-[(3-fluorophenyl)methyl]-1H-pyrrolo[2,3-c]pyridine-2-carboxamide To a solution of 0.25 g (0.82 mmol) of product obtained in step 3.4 in 20 ml of dry dichloromethane are successively added 0.43 g (0.82 mmol) of [(benzotriazol-1-yl)oxy][tris(pyrrolidino)]phosphonium hexafluorophosphate and then 0.17 g (0.98 mmol) of 5-amino-1,2-dimethylbenzimidazole. To this solution is then added dropwise 0.45 ml (2.46 mmol) of N—N-(diisopropyl)ethylamine. The mixture is stirred for 2 hours at room temperature. The pink precipitate formed is filtered off on a sinter funnel and then rinsed several times with dichloromethane and dried under reduced pressure. 0.15 g of the expected product is thus isolated in the form of a white powder.

Melting point: 240-242° C.

$^1$H NMR (DMSO D$_6$), δ (ppm): 10.75 (s, 1H); 8.85 (s, 1H); 7.95 (s, 1H); 7.85 (s, 1H); 7.5 (m, 2H); 7.3 (m, 2H); 6.95 (m, 3H); 5.9 (s, 2H); 3.75 (s, 3H); 2.5 (s, 3H).

EXAMPLE 4

Compound 4

N-(1,2-dimethyl-1H-benzimidazol-5-yl)-1-[(3-fluorophenyl)methyl]-1H-pyrrolo[2,3-c]pyridine-2-carboxamide Hydrochloride (1:2)

1.26 ml (2.51 mmol) of trimethylaluminum (2M in toluene) are added, under nitrogen and with stirring, to a solution of 0.34 g (2 mmol) of 1,2-dimethyl-1H-benzimidazole in 20 ml of dry toluene. After a few minutes, a solution of 0.5 g (1.68 mmol) of ethyl 1-[(3-fluorophenyl)methyl]-1H-pyrrolo[2,3-c]pyridine-2-carboxylate, prepared according to the method described in step 1.3 of Example 1, in 40 ml of dry toluene is added. The reaction medium is refluxed for 3 hours. After cooling to room temperature, it is poured into a mixture of dichloromethane and water. After removing the insoluble material and extracting the aqueous phase with dichloromethane, the combined organic phases are washed, dried and concentrated under reduced pressure. The residue is purified by chromatography on a column of silica gel, eluting with a mixture of dichloromethane and methanol. 0.52 g (1.26 mmol) of the expected product is isolated.

Melting point: 255-257° C.

The corresponding hydrochloride salt is obtained by reacting 0.5 g (1.21 mmol) of product in base form obtained above as a solution in 30 ml of a dichloromethane/methanol mixture (9/1) with 0.7 ml of 4N hydrochloric acid in dioxane. The salt obtained is recrystallized from an ethanol/water mixture (95/5). 0.27 g (0.55 mmol) of the expected product is obtained.

Melting point: 309-310° C.

$^1$H NMR (DMSO D$_6$), δ (ppm): 11.5 (s, NH); 9.6 (s, 1H); 8.4-8.5 (s, 1H); 8.3 (s, 2H); 7.9 (m, 3H); 7.4 (m, 2H); 7.4 (d, 1H); 7.1 (m, 2H); 6.1 (s, 2H); 3.9 (s, 3H), 2.9 (s, 3H).

EXAMPLE 5

Compound 8

N-(1-methyl-1H-indol-5-yl)-1-[(3-fluorophenyl)methyl]-1H-pyrrolo[2,3-b]pyridine-2-carboxamide

5.1 2-(t-butyloxycarbonylamino)-3-methylpyridine 31 g (142.03 mmol) of di-tert-butyl dicarbonate and 35 ml of hexane are placed in a 100 ml three-necked flask equipped with a magnetic stirrer, and are brought to reflux. A solution of 10 g (88.77 mmol) of 2-amino-3-methylpyridine in 10 ml of ethyl acetate is then added dropwise over a period of 2 hours. Refluxing is continued for 1 hour after the end of the addition. After cooling to room temperature, 20 ml of hexane are added and the white precipitate formed after stirring the reaction mixture is collected by filtration, rinsed with hexane and dried under reduced pressure. 15.5 g (74.43 mmol) of white crystals are obtained.

$^1$H NMR (CDCl$_3$), δ (ppm): 8.3 (dd, 1H); 7.5 (dd, 1H); 7.4 (s, NH); 7.1 (ddd, 1H); 2.3 (s, 3H); 1.5 (s, 9H).

5.2 ethyl 1H-pyrrolo[2,3-b]pyridine-2-carboxylate 5 g (24.01 mmol) of product obtained in step 5.1 and 50 ml of dry tetrahydrofuran are placed in a 250 ml three-necked flask equipped with a magnetic stirrer and maintained under a nitrogen atmosphere. 30 ml (48.02 mmol) of a 1.6M solution of butyllithium in THF are added dropwise, while keeping the temperature below 5° C. After stirring for 1 hour at 0° C., the lithiated derivative thus obtained is added to a solution of 7.08 g (48.02 mmol) of diethyl oxalate in 50 ml of dry tetrahydrofuran maintained at a temperature of −3° C. The reaction medium is then allowed to warm to room temperature. The medium is then poured into a solution of 25 ml of 6N hydrochloric acid cooled to 0° C., while keeping the temperature below 10° C. The mixture obtained is then stirred at 50° C. for 2 hours and then at room temperature overnight. The reaction medium is adjusted to pH 3 with sodium hydroxide and is extracted with diethyl ether. The organic phase is dried over sodium sulfate, filtered and evaporated under reduced pressure. 1.8 g (9.46 mmol) of product are obtained, and are used without further purification in the following steps.

$^1$H NMR (CDCl$_3$), δ (ppm): 8.8 (dd, 1H); 8.15 (dd, 1H); 7.2 (m, 2H); 4.5 (q, 2H); 1.5 (t, 3H).

5.3 ethyl 1-[(3-fluorophenyl)methyl]-1H-pyrrolo[2,3-b]pyridine-2-carboxylate Method A: 1.64 g (41.01 mmol) of sodium hydride prewashed with n-pentane, and then 180 ml of dry dimethylformamide are placed in a 500 ml three-necked flask equipped with a magnetic stirrer and maintained under an argon atmosphere. 6 g (31.55 mmol) of product obtained in step 5.2 are added portionwise. The reaction medium is then maintained at 50° C. for 1 hour. A solution of 7.15 g (37.85 mmol) of 3-fluorobenzyl bromide in 10 ml of dry dimethylformamide is then added dropwise. The reaction mixture is then stirred at reflux for 16 hours. The cooled solution is diluted in a mixture of 200 ml of ice-water and 200 ml of ethyl acetate. After separation of the phases by settling, the aqueous phase is extracted with ethyl acetate and the combined organic phases are successively washed with 100 ml of water and 100 ml of saturated aqueous sodium chloride solution, dried over sodium sulfate and then concentrated under reduced pressure. The resulting oil is purified by chromatography on a column of silica, eluting with a mixture of dichloromethane and n-heptane. 5.73 g of product are obtained, and are used without further purification in the following steps.

Method B: To a solution of 5.2 g (27.34 mmol) of product obtained in step 5.2, in 250 ml of dry tetrahydrofuran, maintained under an inert atmosphere, are successively added with stirring 5.28 g (41 mmol) of 3-fluorobenzyl alcohol and then 10.87 g (41 mmol) of triphenylphosphine. 7.36 g (41 mmol) of diethyl azodicarboxylate are then added dropwise at 0° C. The reaction mixture is then stirred for 20 hours at room temperature and then concentrated under reduced pressure. A mixture of pentane and diethyl ether is added and the precipitate is removed by filtration. After concentrating under reduced pressure, the resulting oil is purified by successive chromatographies on a column of silica gel. 6.2 g of product are isolated.

$^1$H NMR (CDCl$_3$), δ (ppm): 8.6 (dd, 1H); 8.1 (dd, 1H); 7.4 (s, 1H); 7.2 (m, 2H); 6.95 (m, 3H); 6.0 (s, 2H); 4.4 (q, 2H); 1.4 (t, 3H).

5.4 N-(1-methyl-1H-indol-5-yl)-1-[(3-fluorophenyl)methyl]-1H-pyrrolo[2,3-b]pyridine-2-carboxamide A solution of 0.31 g (1.75 mmol) of 5-amino-1-methylindole in 10 ml of dry toluene is added, without heating, under argon and with magnetic stirring, to a solution of 1.75 ml (3.50 mmol) of trimethylaluminum in 5 ml of dry toluene. The reaction medium is maintained at 50° C. for 2 hours. 0.52 g (1.75 mmol) of ester obtained in step 5.3 dissolved in toluene is then added and the solution is refluxed for 5 hours. Ethyl acetate, ice-water and then 1N hydrochloric acid are added to the cooled solution. After separation of the phases by settling, the aqueous phase is extracted with ethyl acetate. The combined organic phases are washed with water and with saturated sodium chloride solution, dried and concentrated under reduced pressure. The residue is purified by chromatography on a column of silica, eluting with a mixture of dichloromethane and ethyl acetate. The solid is taken up in a solution of sodium hydroxide and ethyl acetate, and the organic phase is dried over sodium sulfate and concentrated under reduced pressure. The solid obtained is triturated from petroleum ether, collected by filtration and dried under reduced pressure. 0.56 g of the expected product is isolated.

Melting point: 191-191.5° C.
$^1$H NMR (DMSO D$_6$), δ (ppm): 10.3 (s, 1H); 8.45 (dd, 1H); 8.2 (dd, 1H); 7.95 (s, 1H); 7.35 (m, 3H); 7.25 (m, 3H); 6.95 (m, 3H); 6.4 (d, 1H); 5.95 (s, 2H); 3.75 (s, 3H).

EXAMPLE 6

Compound 9

N-(1-methyl-1H-benzimidazol-5-yl)-1-[(3-fluorophenyl)methyl]-1H-pyrrolo[2,3-b]pyridine-2-carboxamide Hydrochloride (2:3)

The process is performed according to the method described in step 5.4 of Example 5, starting with 0.5 g (1.68 mmol) of ethyl 1-[(3-fluorophenyl)methyl]-1H-pyrrolo[2,3-b]pyridine-2-carboxylate prepared according to the method described in step 5.3 of Example 5, 1.68 ml (3.35 mmol) of 2M trimethylaluminum in toluene and 0.30 g (2.01 mmol) of 5-amino-1-methylbenzimidazole. After refluxing for 3 hours and reacting overnight at room temperature, ice-water and 1N hydrochloric acid are added. The precipitate is collected by filtration, washed with water and dried under reduced pressure. 0.42 g (1.05 mmol) of product is isolated, and is taken up in 15 ml of diethyl ether, to which are added 1.1 ml of 2N hydrochloric acid in diethyl ether. The mixture is stirred overnight at room temperature and the solid is collected by filtration, washed with diethyl ether and dried under reduced pressure. 0.48 g of the expected product is obtained in the form of the hydrochloride.

Melting point: 171-177° C.
$^1$H NMR (DMSO D$_6$), δ (ppm): 10.85 (s, NH); 9.5 (s, 1H); 8.45 (m, 2H); 8.25 (dd, 1H); 7.9 (m, 2H); 7.6 (s, 1H); 7.3 (m, 2H); 6.9 (m, 3H); 5.9 (s, 2H); 4.0 (s, 3H).

EXAMPLE 7

Compound 10

N-(2-oxo-1,2,3,4-tetrahydroquinol-7-yl)-1-[(3-fluorophenyl)methyl]-1H-pyrrolo[2,3-b]pyridine-2-carboxamide 0.33 g (2.01 mmol) of 7-amino-3,4-dihydroquinolin-2(1H)-one is added portionwise, under argon and with magnetic stirring, to a solution of 2.51 ml (5.03 mmol) of trimethylaluminum in 20 ml of dry toluene. The reaction medium is maintained at 50° C. for 30 minutes. 0.5 g (1.68 mmol) of ester obtained in step 5.3 of Example 5 dissolved in 5 ml of toluene is then added slowly and the solution is refluxed for 2 hours. Water and dilute hydrochloric acid are added to the cooled solution. The precipitate is collected by filtration, washed with water and dried under reduced pressure. The residue is taken up in dichloromethane and the organic phase is washed with water and with saturated sodium chloride solution, dried and concentrated under reduced pressure. The residue is purified by chromatography on a column of silica, eluting with a mixture of dichloromethane and methanol. 0.48 g (1.16 mmol) of the expected product is isolated.

Melting point: 280-282° C.
$^1$H NMR (DMSO D$_6$), δ (ppm): 10.45 (s, NH); 10.1 (s, NH); 8.45 (d, 1H); 8.2 (d, 1H); 7.4 (m, 2H); 7.3-6.8 (m, 7H); 5.9 (s, 2H); 2.8 (t, 2H); 2.4 (t, 2H).

EXAMPLE 8

Compound 11

N-(quinol-7-yl)-1-[(3-fluorophenyl)methyl]-1H-pyrrolo[2,3-b]pyridine-2-carboxamide Hydrochloride (1:1)

8.1 1-[(3-fluorophenyl)methyl]-1H-pyrrolo[2,3-b]pyridine-2-carboxylic Acid

A solution of 0.6 g (2.01 mmol) of ester obtained in step 5.3. and 0.23 g (4.02 mmol) of potassium hydroxide in 60 ml of methanol is refluxed for 2 hours. The solution is concentrated under reduced pressure and the residue is taken up in water and acidified with dilute hydrochloric acid. The precipitate is collected by filtration, washed with water and dried under reduced pressure. 0.37 g of product is obtained, and is used without further purification in the following steps.

8.2 N-(quinol-7-yl)-1-[(3-fluorophenyl)methyl]-1H-pyrrolo[2,3-b]pyridine-2-carboxamide Hydrochloride (1:1)

0.37 g (1.37 mmol) of acid obtained in step 8.1, 40 ml of dichloromethane and 1 ml (13.69 mmol) of thionyl chloride are placed in a 100 ml round-bottomed flask equipped with a magnetic stirrer. The suspension thus obtained is refluxed for 2 hours. After evaporating off the solvent under reduced pressure, 50 ml of dry ether, 0.35 g (1.64 mmol) of 7-aminoquinoline dihydrochloride (WO03/068 749) and a solution of 0.58 g (5.48 mmol) of sodium carbonate in 5 ml of water are added. The reaction medium is stirred overnight and the organic solvent is evaporated off under reduced pressure. Water is added and the precipitate is collected by filtration. The solid obtained is taken up in dichloromethane and the organic phase is washed with water and with saturated sodium chloride solution, dried over sodium sulfate and concentrated under reduced pressure. The residue is purified by chromatography on a column of silica gel, eluting with a mixture of dichloromethane and ethanol (95/5). The product is taken up in 20 ml of diethyl ether and 1 ml of 2N hydrochloric acid in diethyl ether, and the solution is then stirred overnight. The solid is collected by filtration and washed with diethyl ether. It is washed again with hot ethanol. After cooling to room temperature, it is collected by filtration and oven-dried under reduced pressure. 0.19 g of the expected product is obtained.

Melting point: 260-262° C.

$^1$H NMR (DMSO D$_6$), δ (ppm): 11.2 (s, 1H); 9.15 (d, 1H); 8.9 (m, 2H); 8.5 (m, 1H); 8.3 (m, 2H); 8.15 (m, 1H); 7.85 (m, 1H); 7.65 (s, 1H); 7.3 (m, 2H); 6.9 (m, 3H); 6.0 (s, 2H).

EXAMPLE 9

Compound 12

N-(1-methyl-1H-indol-5-yl)-1-(phenylmethyl)-1H-pyrrolo[2,3-b]pyridine-2-carboxamide Ethyl 1-(phenylmethyl)-1H-pyrrolo[2,3-b]pyridine-2-carboxylate is prepared beforehand according to the method described in Example 5.3B, starting with the product obtained in Example 5.2 and benzyl alcohol. The process is then performed according to the method described in step 5.4 of Example 5, starting with ethyl 1-(phenylmethyl)-1H-pyrrolo[2,3-b]pyridine-2-carboxylate (1 eq), 2M trimethylaluminum in toluene (1.5 eq) and 5-amino-1-methylindole (1.2 eq). The crude reaction product is purified by chromatography on a column of silica gel.

Melting point: 181-182° C.

$^1$H NMR (DMSO D$_6$), δ (ppm): 10.3 (1H, NH); 8.45 (d, 1H); 8.2 (d, 1H); 7.95 (s, 1H); 7.4-7.05 (m, 10H); 6.4 (d, 1H); 5.95 (s, 2H), 3.8 (s, 3H).

EXAMPLE 10

Compound 13

N-(1-methyl-1H-indol-5-yl)-1-(phenylethyl)-1H-pyrrolo[2,3-b]pyridine-2-carboxamide Ethyl 1-(phenylethyl)-1H-pyrrolo[2,3-b]pyridine-2-carboxylate is prepared beforehand according to the method described in Example 5.3B, starting with the product obtained in Example 5.2 and 2-phenylethanol. The process is then performed according to the method described in step 5.4 of Example 5, starting with ethyl 1-(phenylethyl)-1H-pyrrolo[2,3-b]pyridine-2-carboxylate (1 eq), 2M trimethylaluminum in toluene (1.5 eq) and 5-amino-1-methylindole (1.2 eq). The crude reaction product is purified by chromatography on a column of silica gel.

Melting point: 196-199° C.

$^1$H NMR (DMSO D$_6$), δ (ppm): 10.25 (s, NH); 8.45 (d, 1H); 8.15 (dd, 1H); 8.0 (s, 1H); 7.5-7.1 (m, 10H); 6.45 (d, 1H); 4.9 (t, 2H); 3.8 (s, 3H); 3.05 (t, 2H).

EXAMPLE 11

Compound 14

N-(2-methyl-benzothiazol-5-yl)-1-[(3-fluorophenyl)methyl]-1H-pyrrolo[2,3-b]pyridine-2-carboxamide Hydrochloride (2:3)

1.68 ml (3.35 mmol) of a 2M solution of trimethylaluminum in toluene and 20 ml of dry toluene are placed, while flushing with nitrogen, in a 100 ml round-bottomed flask cooled to 0° C. and equipped with a magnetic stirrer. 0.33 g (2.01 mmol) of 5-amino-2-methylbenzothiazole is then added portionwise. The reaction mixture is maintained at 50° C. for 30 minutes and a solution of 0.5 g (1.68 mmol) of ester obtained in step 5.3 in 20 ml of dry toluene is then added dropwise over 5 minutes. The reaction mixture is then refluxed for 4 hours. 50 ml of ice-water and 20 ml of ethyl acetate are then added to the solution cooled to 0° C. After stirring for 30 minutes, the solid formed is removed by filtration and washed with water and with ethyl acetate. After separation of the phases by settling, the aqueous phase is extracted with ethyl acetate and the combined organic phases are successively washed with water and with saturated aqueous sodium chloride solution, dried over sodium sulfate and then concentrated under reduced pressure. The resulting solid is purified by chromatography on a column of silica, eluting with a mixture of dichloromethane and ethyl acetate. The corresponding hydrochloride is prepared by treatment with a solution of hydrochloric acid in diethyl ether. 0.475 g of the expected product is isolated.

Melting point: 211-212° C.

$^1$H NMR (DMSO D$_6$), δ (ppm): 10.65 (s, 1H); 8.5 (dd, 1H); 8.4 (d, 1H); 8.2 (dd, 1H); 7.95 (d, 1H); 7.75 (dd, 1H); 7.5 (s, 1H); 7.3 (m, 2H); 6.9 (m, 3H); 5.9 (s, 2H); 2.8 (s, 3H).

EXAMPLE 12

Compound 15

N-(1-methyl-1H-benzimidazol-5-yl)-5-fluoro-1-[(3-fluorophenyl)methyl]-1H-pyrrolo[2,3-b]pyridine-2-carboxamide

12.1 2-amino-3-iodo-5-fluoropyridine 5 g (44.6 mmol) of 2-amino-5-fluoropyridine, 13.9 g (44.6 mmol) of silver sulfate and 400 ml of ethanol are placed in a 500 ml two-necked flask equipped with a magnetic stirrer. 11.31 g (44.6 mmol) of iodine powder are then added portionwise. Stirring is continued at room temperature for 24 hours. The resulting yellow suspension is filtered, the precipitate is rinsed with ethanol and the filtrate is concentrated under reduced pressure. The residue thus obtained is taken up in a mixture of ethyl acetate (200 ml) and sodium carbonate solution (200 ml). After separation, the organic phase is successively washed with aqueous 25% sodium thiosulfate solution, with saturated aqueous sodium chloride solution and then dried over sodium sulfate and concentrated under reduced pressure. The resulting solid is purified by chromatography on a column of silica, eluting with a mixture of n-heptane and ethyl acetate. 2.67 g (11.22 mmol) of the expected product are obtained.

$^1$H NMR (DMSO D$_6$), δ (ppm): 7.95 (s, 1H); 7.85 (s, 1H); 5.9 (s, NH2).

12.2
5-fluoro-1H-pyrrolo[2,3-b]pyridine-2-carboxylic Acid 0.5 g (2.10 mmol) of 2-amino-3-iodo-5-fluoropyridine obtained in step 12.1, 0.55 g (6.3 mmol) of pyruvic acid, 0.71 g (6.3 mmol) of 1,4-diazabicyclo[2.2.2]octane (DABCO) and 15 ml of anhydrous dimethylformamide are placed in a 25 ml sealed tube equipped with a magnetic stirrer and maintained under an argon sparge. After a few minutes, 0.05 g (0.22 mmol) of palladium acetate is added. The reaction mixture is stirred for 20 minutes while sparging with argon and is then rapidly sealed and maintained at 100° C. for 2 hours 30 minutes. The cooled solution is concentrated to dryness under reduced pressure. The residue is then taken up in ethyl acetate (100 ml) and water (75 ml). The organic phase is washed with water and then extracted with twice 50 ml of aqueous 2N sodium hydroxide solution. The basic aqueous phases are combined, cooled to 0° C. and then acidified by adding hydrochloric acid (pH 3). The medium is extracted with ethyl acetate (4×50 ml) and the combined organic phases are dried over sodium sulfate and then concentrated under reduced pressure. 0.158 g (0.88 mmol) of the expected product is obtained in the form of a yellow powder.

$^1$H NMR (DMSO D$_6$), δ (ppm): 13.2 (s, 1H); 12.4 (s, 1H); 8.4 (d, 1H); 7.95 (dd, 1H); 7.1 (d, 1H).

12.3 ethyl 5-fluoro-1H-pyrrolo[2,3-b]pyridine-2-carboxylate 0.2 g (1.11 mmol) of acid obtained in step 12.2 and 10 ml of ethanol are placed in a 100 ml round-bottomed flask equipped with a magnetic stirrer. 1 ml of concentrated sulfuric acid is added to the reaction mixture, which is then refluxed for 18 hours. The cooled solution is concentrated to dryness under reduced pressure. The residue is taken up in ethyl acetate (50 ml) and washed successively with aqueous normal sodium hydroxide solution (2×10 ml), with water (10 ml) and then with saturated aqueous sodium chloride solution. The organic phase is dried over sodium sulfate and then concentrated under reduced pressure. 0.21 g of the expected product is isolated.

$^1$H NMR (DMSO D$_6$), δ (ppm): 12.6 (s, NH); 8.4 (d, 1H); 8.0 (dd, 1H); 7.1 (d, 1H); 4.35 (q, 2H); 1.35 (t, 3H).

12.4 ethyl 5-fluoro-1-[(3-fluorophenyl)methyl]-1H-pyrrolo[2,3-b]pyridine-2-carboxylate To a solution of 0.2 g (0.96 mmol) of product obtained in step 12.3, in 15 ml of dry tetrahydrofuran, maintained under an inert atmosphere, are successively added with stirring 0.18 g (1.44 mmol) of 3-fluorobenzyl alcohol and then 0.39 g (1.44 mmol) of triphenylphosphine. 0.26 g (1.44 mmol) of diethyl azodicarboxylate is then added dropwise at 0° C. The reaction mixture is then stirred for 20 hours at room temperature and then concentrated under reduced pressure. The resulting oil is purified by chromatography on a column of silica gel, eluting with a mixture of dichloromethane and methanol. 0.26 g (0.82 mmol) of the expected product is isolated.

12.5 N-(1-methyl-1H-benzimidazol-5-yl)-5-fluoro-1-[(3-fluorophenyl)methyl]-1H-pyrrolo[2,3-b]pyridine-2-carboxamide 0.18 g (1.23 mmol) of 5-amino-1-methylbenzimidazole and 10 ml of dry toluene are placed, while flushing with nitrogen, in a 100 ml three-necked flask cooled to 0° C. and equipped with a magnetic stirrer. To this solution is then added slowly 0.95 ml (1.90 mmol) of a 2M solution of trimethylaluminum in toluene. The reaction mixture obtained is maintained under a nitrogen atmosphere and stirred, while allowing the temperature to rise gradually to 70° C. A solution of 0.3 g (0.95 mmol) of product obtained in step 12.4 in 10 ml of dry toluene is then added dropwise over 5 minutes using an addition funnel. The reaction mixture is then refluxed for 5 hours and stirred at room temperature overnight. 20 ml of cold water are then added to the solution cooled to 0° C., followed by addition of 10 ml of 1N hydrochloric acid. After stirring for 1 hour, the precipitate is recovered by filtration, rinsed with water and dried under reduced pressure. 0.22 g (0.53 mmol) of the expected product is obtained in the form of a white solid.

Melting point: 266-268° C.
$^1$H NMR (DMSO D$_6$), δ (ppm): 9.5 (s, 1H); 8.5 (s, 1H); 7.9 (s, 2H); 7.5 (m, 3H); 7.3-6.8 (m, 5H); 5.9 (s, 2H); 3.95 (s, 3H).

EXAMPLE 13

Compound 16

N-(1,2-dimethyl-1H-benzimidazol-5-yl)-5-trifluoromethyl-1-[(3-fluorophenyl)methyl]-1H-pyrrolo[2,3-b]pyridine-2-carboxamide

13.1 2-amino-3-iodo-5-(trifluoromethyl)pyridine 2 g (12.34 mmol) of 2-amino-5-trifluoromethylpyridine, 3.85 g (12.34 mmol) of silver sulfate and 80 ml of ethanol are placed in a 500 ml two-necked flask equipped with a magnetic stirrer. 3.13 g (12.34 mmol) of iodine powder are then added portionwise to the reaction medium stirred at room temperature. The reaction mixture is then stirred at room temperature for 48 hours. The resulting yellow suspension is filtered, the precipitate is rinsed with ethanol and the filtrate is evaporated under reduced pressure. The residue thus obtained is taken up in dichloromethane (200 ml). The organic phase is washed successively with aqueous 5% sodium hydroxide solution, with water and then with saturated aqueous sodium chloride solution. It is dried over sodium sulfate and concentrated under reduced pressure. The resulting solid is purified by chromatography on a column of silica, eluting with a mixture of n-heptane and ethyl acetate. 1.71 g (5.94 mmol) of product are obtained in the form of a pink powder.

$^1$H NMR (DMSO D$_6$), δ (ppm): 8.3 (s, 1H); 8.1 (s, 1H); 6.8 (s, NH2).

13.2 5-trifluoromethyl-1H-pyrrolo[2,3-b]pyridine-2-carboxylic Acid 2 g (6.94 mmol) of product obtained in step 13.1, 1.51 g (20.83 mmol) of pyruvic acid, 2.41 g (20.83 mmol) of 1,4-diazabicyclo[2.2.2]octane (DABCO) and 20 ml of anhydrous dimethylformamide are placed in a 25 ml sealed tube equipped with a magnetic stirrer and maintained under an argon sparge. After a few minutes, 2 g (8.91 mmol) of palladium acetate are added. The reaction mixture is stirred for 20 minutes while sparging with argon and then rapidly sealed and maintained at 110° C. for 6 hours. The cooled solution is concentrated to dryness under reduced pressure. The residue is taken up in ethyl acetate and water. After separation of the phases by settling, the organic phase is extracted with twice 50 ml of aqueous 2N sodium hydroxide solution. The basic aqueous phases are combined, cooled to 0° C. and then acidified by adding hydrochloric acid (pH 3). The aqueous phase is extracted with ethyl acetate (4×50 ml) and the combined organic phases are dried over sodium sulfate and then concentrated under reduced pressure. 0.67 g (2.91 mmol) of the expected product are obtained in the form of a yellow powder, which is used without further purification in the following steps.

$^1$H NMR (DMSO $D_6$), δ (ppm): 12.8 (s, 1H); 8.7 (d, 1H); 8.5 (d, 1H); 7.2 (s, 1H).

13.3 ethyl 5-trifluoromethyl-1H-pyrrolo[2,3-b]pyridine-2-carboxylate 0.3 g (1.3 mmol) of the acid obtained in step 13.2 and 50 ml of ethanol are placed in a 100 ml round-bottomed flask equipped with a magnetic stirrer. 0.5 ml of concentrated sulfuric acid is added to this solution. The reaction mixture is then refluxed for 18 hours. The cooled solution is concentrated to dryness under reduced pressure. The residue is taken up in dichloromethane (100 ml) and the organic phase is successively washed with aqueous normal sodium hydroxide solution (30 ml), with water (20 ml) and then with saturated aqueous sodium chloride solution. It is dried over sodium sulfate and then concentrated under reduced pressure. 0.29 g (1.12 mmol) of the expected product is isolated in the form of a yellow powder.

$^1$H NMR (DMSO $D_6$), δ (ppm): 12.95 (s, NH); 8.8 (d, 1H); 8.6 (d, 1H); 7.3 (s, 1H); 4.4 (q, 2H); 1.35 (t, 3H).

13.4 ethyl 5-trifluoromethyl-1-[(3-fluorophenyl)methyl]-1H-pyrrolo[2,3-b]pyridine-2-carboxylate To a solution of 0.3 g (1.16 mmol) of product obtained in step 13.3, in 20 ml of dry tetrahydrofuran, maintained under an inert atmosphere, are successively added with stirring 0.23 g (1.74 mmol) of 3-fluorobenzyl alcohol and then 0.46 g (1.74 mmol) of triphenylphosphine. 0.31 g (1.74 mmol) of diethyl azodicarboxylate is then added dropwise. The reaction mixture is then stirred for 20 hours at room temperature and then concentrated under reduced pressure. The resulting oil is purified by chromatography on a column of silica gel, eluting with a mixture of heptane and ethyl acetate. 0.34 g (0.93 mmol) of the expected product is isolated.

$^1$H NMR (DMSO $D_6$), δ (ppm): 8.9 (d, 1H); 8.7 (d, 1H); 7.5 (s, 1H); 7.4-6.95 (m, 2H); 6.85 (m, 2H); 5.9 (s, 2H); 4.3 (q, 2H), 1.3 (t, 3H).

13.5 N-(1,2-dimethyl-1H-benzimidazol-5-yl)-5-trifluoromethyl-1-[(3-fluorophenyl)methyl]-1H-pyrrolo[2,3-b]pyridine-2-carboxamide 0.17 g (1 mmol) of 5-amino-1,2-dimethylbenzimidazole and 10 ml of dry toluene are placed, while flushing with nitrogen, in a 100 ml three-necked flask cooled to 0° C. and equipped with a magnetic stirrer. 0.77 ml (1.54 mmol) of a 2M solution of trimethylaluminum in toluene is then added slowly to this solution. The reaction mixture obtained is maintained under a nitrogen atmosphere and stirred while allowing the temperature to rise gradually to 70° C. At this temperature, a solution of 0.3 g (0.77 mmol) of product obtained in step 13.4 in 10 ml of dry toluene is added dropwise over 5 minutes. The reaction mixture is then refluxed for 4 hours. 20 ml of cold water are then added to the solution cooled to 0° C. After stirring for 90 minutes, the precipitate formed is extracted three times with ethyl acetate (3×50 ml) and the combined organic phases are successively washed with 20 ml of saturated aqueous sodium hydrogen carbonate solution, 40 ml of water and 20 ml of saturated aqueous sodium chloride solution, dried over sodium sulfate and then concentrated under reduced pressure. The resulting solid is purified by chromatography on a column of silica, eluting with a mixture of dichloromethane and methanol. The solid obtained is recrystallized from an isopropanol/ethanol mixture (9/1) to give 0.23 g (0.48 mmol) of the expected product in the form of white crystals.

Melting point: 263-265° C.

$^1$H NMR (DMSO $D_6$), δ (ppm): 11 (s, 1H); 8.85 (s, 1H); 8.75 (s, 1H); 8.3 (s, 1H); 7.9 (m, 2H); 7.7 (s, 1H); 7.3 (m, 1H); 6.95 (m, 3H); 5.95 (s, 2H); 3.9 (s, 3H); 2.8 (s, 3H).

EXAMPLE 14

Compound 18

N-(2-methyl-1H-benzothiazol-5-yl)-5-trifluoromethyl-1-[(3-fluorophenyl)methyl]-1H-pyrrolo[2,3-b]pyridine-2-carboxamide The process is performed according to the method described in step 13.5 of Example 13, starting with 0.35 g (0.96 mmol) of ethyl 5-trifluoromethyl-1-[(3-fluorophenyl)methyl]-1H-pyrrolo[2,3-b]pyridine-2-carboxylate (Example 13.4) and 0.17 g (1.06 mmol) of 5-amino-2-methylbenzothiazole. 0.34 g of expected compound is isolated.

Melting point: 204-206° C.

$^1$H NMR (DMSO $D_6$), δ (ppm): 10.78 (s, 1H); 8.8 (s, 1H); 8.7 (s, 1H); 8.31 (s, 1H); 7.97 (d, 1H); 7.71 (d, 1H); 7.6 (s, 1H); 7.28 (m, 1H); 6.95 (m, 3H); 5.95 (d, 2H); 2.8 (s, 3H).

EXAMPLE 15

Compound 19

N-(1,2-dimethyl-1H-benzimidazol-5-yl)-1-[(3-fluorophenyl)methyl]-1H-pyrrolo[2,3-b]pyridine-2-carboxamide The process is performed according to the method described in Example 11, starting with 0.4 g (1.34 mmol) of ethyl 1-[(3-fluorophenyl)methyl]-1H-pyrrolo[2,3-b]pyridine-2-carboxylate (Example 5.3) and 0.25 g (1.61 mmol) of 5-amino-1,2-dimethylbenzimidazole. 0.477 g of expected compound is isolated.

Melting point: 242-244° C.

$^1$H NMR (DMSO $D_6$), δ (ppm): 2.49 (s, 3H); 3.69 (s, 3H); 5.91 (s, 2H); 6.94 (m, 3H); 7.22 (m, 2H); 7.39 (m, 3H); 7.79 (s, 1H); 8.19 (dxd, 1H); 8.41 (d, 1H); 10.31 (s, 1H).

EXAMPLE 16

Compound 6

N-(1,2-dimethyl-1H-benzimidazol-5-yl)-5-fluoro-1-[(3-fluorophenyl)methyl]-1H-pyrrolo[2,3-c]pyridine-2-carboxamide The process is performed according to the method described in step 2.4 of Example 2, starting with 0.3 g (0.95 mmol) of ethyl 5-fluoro-1-[(3-fluorophenyl)methyl]-1H-pyrrolo[2,3-c]pyridine-2-carboxylate (Example 2.3) and 0.183 g (1.14 mmol) of 5-amino-1,2-dimethylbenzimidazole. 0.21 g of expected compound is isolated.

Melting point: 245-247° C.
$^1$H NMR (DMSO D$_6$), δ (ppm): 10.59 (s, 1H); 8.62 (s, 1H); 7.91 (s, 1H); 7.4 (m, 5H); 7.01 (m, 3H); 5.91 (s, 2H); 3.71 (s, 3H); 2.49 (s, 3H).

EXAMPLE 17

Compound 5

N-(2-methyl-1H-benzothiazol-5-yl)-5-fluoro-1-[(3-fluorophenyl)methyl]-1H-pyrrolo[2,3-c]pyridine-2-carboxamide The process is performed according to the method described in step 2.4 of Example 2, starting with 0.3 g (0.95 mmol) of ethyl 5-fluoro-1-[(3-fluorophenyl)methyl]-1H-pyrrolo[2,3-c]pyridine-2-carboxylate (Example 2.3) and 0.189 mg (1.14 mmol) of 5-amino-2-methylbenzothiazole. 0.36 g of expected compound is isolated.

Melting point: 193-195° C.
$^1$H NMR (DMSO D$_6$), δ (ppm): 10.87 (s, 1H); 8.68 (s, 1H); 8.32 (s, 1H); 7.98 (d, 1H); 7.71 (d, 1H); 7.35 (m, 3H); 6.99 (m, 3H); 5.9 (s, 2H); 2.79 (s, 3H).

EXAMPLE 18

Compound 7

N-(1,2-dimethyl-1H-benzimidazol-5-yl)-5-phenyl-1-[(3-fluorophenyl)methyl]-1H-pyrrolo[2,3-c]pyridine-2-carboxamide

18.1 4-methyl-5-nitro-2-phenylpyridine

A mixture of 2 g (11.59 mmol) of 2-chloro-4-methyl-5-nitropyridine, 1.41 g (11.59 mmol) of phenylboronic acid, 1.33 g (1.16 mmol) of tetrakis(triphenylphosphine)palladium and 4 g (28.97 mmol) of potassium carbonate suspended in 50 ml of degassed dioxane is refluxed for 12 hours. The mixture is then cooled, diluted with 50 ml of ethyl acetate, successively washed twice with 20 ml of water and then with 20 ml of saturated sodium chloride solution, dried over sodium sulfate, filtered and then concentrated under reduced pressure. The residue obtained is purified by chromatography on a column of silica (eluents: heptane/ethyl acetate) and then recrystallized from an isopropanol/isopropyl ether mixture. 2.19 g of a yellow solid are thus isolated, and are used without further purification in the following synthesis.

18.2 ethyl 3-(5-nitro-2-phenyl-4-pyridyl)-2-oxopropionate

A mixture of 1.3 g (6.07 mmol) of 4-methyl-3-nitro-2-phenylpyridine, obtained in step 18.1, and 1.01 g (6.68 mmol) of 1,8-diazabicyclo[5.4.0]undec-7-ene in 4.14 ml of diethyl oxalate is stirred at room temperature for 4 hours. After this time, the mixture is diluted with 30 ml of ethyl acetate, 20 ml of water and 2 ml of acetic acid. The solution obtained is extracted twice with 50 ml of ethyl acetate. The combined organic phases are successively washed twice with 20 ml of water and then with 20 ml of saturated sodium chloride solution, dried over sodium sulfate, filtered and then concentrated under reduced pressure. The residue obtained is purified by chromatography on a column of silica (eluents: heptane/ethyl acetate). 1.46 g of the expected product are thus isolated in the form of a white solid.

18.3 ethyl 5-phenyl-1H-pyrrolo[2,3-c]pyridine-2-carboxylate

A mixture of 1.3 g (4.3 mmol) of ethyl 3-(5-nitro-2-phenyl-4-pyridyl)-2-oxopropionate, obtained in step 18.2, and 0.71 g (12.89 mmol) of iron powder in a mixture of 20 ml of saturated ammonium chloride solution, 20 ml of tetrahydrofuran and 40 ml of ethanol is refluxed for three hours. The reaction mixture is then cooled and filtered through a plug of Celite. The filtrate is concentrated to one third of its volume under reduced pressure and then extracted three times with 50 ml of ethyl acetate. The combined organic phases are successively washed twice with 20 ml of water and then 20 ml of saturated sodium chloride solution, dried over sodium sulfate, filtered and then concentrated under reduced pressure. The residue obtained is purified by chromatography on a column of silica (eluents: heptane/ethyl acetate). 0.93 g of the expected product is thus isolated in the form of a beige powder.

18.4 ethyl 5-phenyl-1-[(3-fluorophenyl)methyl]-1H-pyrrolo[2,3-c]pyridine-2-carboxylate 0.72 g (5.63 mmol) of 3-fluorobenzyl alcohol, 1.47 g (5.63 mmol) of triphenylphosphine and then 1.01 g (5.63 mmol) of diethyl azodicarboxylate are successively added to a solution, stirred at 0° C. under argon, of 1 g (3.76 mmol) of ethyl 5-phenyl-1H-pyrrolo[2,3-c]pyridine-2-carboxylate, obtained in step 18.3, in 30 ml of dry tetrahydrofuran. The mixture is then stirred for 20 hours at 20° C., concentrated under reduced pressure and then purified by chromatography on a column of silica (eluents: heptane/ethyl acetate). 1.1 g of the expected product are thus isolated in the form of a white powder.

18.5 N-(1,2-dimethyl-1H-benzimidazol-5-yl)-5-phenyl-1-[(3-fluorophenyl)methyl]-1H-pyrrolo[2,3-c]pyridine-2-carboxamide (Compound 7)

0.217 g (1.35 mmol) of 5-amino-1,2-dimethylbenzimidazole and 5 ml of dry toluene are placed, while flushing with nitrogen, in a 100 ml three-necked flask cooled to 0° C. and equipped with a magnetic stirrer. 0.84 ml (1.68 mmol) of a 2M solution of trimethylaluminum in toluene is then added slowly to this solution. The reaction mixture obtained is maintained under a nitrogen atmosphere and stirred while allowing the temperature to rise gradually to 70° C. At this temperature, a solution of 0.42 g (1.12 mmol) of ethyl 5-phenyl-1-[(3-fluorophenyl)methyl]-1H-pyrrolo[2,3-c]pyridine-2-carboxylate, obtained in step 18.4, in 10 ml of dry toluene is added dropwise over 5 minutes. The reaction mixture is then refluxed for 4 hours. 20 ml of cold water are then added to the solution cooled to 0° C. After stirring for 90 minutes, the solution is extracted three times with ethyl acetate (3×50 ml) and the combined organic phases are successively washed with 20 ml of saturated aqueous sodium hydrogen carbonate solution, 40 ml of water and 20 ml of saturated aqueous sodium chloride solution, dried over sodium sulfate and then concentrated under reduced pressure. The resulting solid is triturated from boiling isopropyl ether and then recrystallized from an isopropanol/methanol mixture (9/1) to give 0.187 g of the expected product in the form of a beige powder.

Melting point: 288-290° C.

$^1$H NMR (DMSO D$_6$), δ (ppm): 10.6 (s, 1H); 9.08 (s, 1H); 8.27 (s, 1H); 8.1 (d, 2H); 7.98 (s, 1H); 7.41 (m, 7H); 7.01 (m, 3H); 5.98 (s, 2H); 3.71 (s, 3H); 2.48 (s, 3H).

EXAMPLE 19

Compound 24

N-(1,2-dimethyl-1H-benzimidazol-5-yl)-5-trifluoromethyl-1-[(3-fluorophenyl)methyl]-1H-pyrrolo[3,2-b]pyridine-2-carboxamide 19.1 3-amino-2-iodo-6-trifluoromethylpyridine 1.56 g (6.17 mmol) of iodine are added portionwise to a mixture, stirred under argon at 20° C., of 1 g (6.17 mmol) of 3-amino-6-trifluoromethylpyridine and 1.25 g (6.17 mmol) of silver sulfate in 40 ml of ethanol. Stirring is continued for 18 hours. The resulting yellow suspension is filtered and rinsed with ethanol. The filtrate is concentrated under reduced pressure and the residue is taken up in 100 ml of dichloromethane. The organic phase is successively washed with 20 ml of aqueous 5% sodium hydroxide solution, 40 ml of water and 20 ml of saturated aqueous sodium chloride solution, dried over sodium sulfate, concentrated under reduced pressure and then purified by chromatography on a column of silica (eluents: heptane/ethyl acetate). 1.17 g of the expected product are thus isolated, and are used without further purification in the following synthesis.

19.2 5-trifluoromethylpyrrolo[3,2-b]pyridine-2-carboxylic acid 0.5 g (1.74 mmol) of 3-amino-2-iodo-6-trifluoromethylpyridine, obtained in step 19.1, 0.45 g (5.21 mmol) of pyruvic acid, 0.51 ml (5.21 mmol) of 1,4-diazabicyclo[2.2.2]octane and 10 ml of dry dimethylformamide are placed in a sealed tube under argon. The solution is degassed for a few minutes, 0.19 g (0.87 mmol) of palladium acetate is then added and the tube is closed and refluxed for 4 hours at 130° C. The cooled solution is then concentrated under reduced pressure and the resulting residue is taken up in 100 ml of ethyl acetate. The organic phase is successively washed with twice 50 ml of aqueous 2N sodium hydroxide solution. The basic aqueous phases are combined, cooled to 0° C., acidified by addition of hydrochloric acid and then extracted with 4 times 50 ml of ethyl acetate. These organic phases are combined, washed with 20 ml of saturated aqueous sodium chloride solution, dried over sodium sulfate and then concentrated under reduced pressure. 0.22 g of product is obtained, and is used without further purification in the following step.

19.3 ethyl 5-trifluoromethylpyrrolo[3,2-b]pyridine-2-carboxylate 1 ml (18.71 mmol) of concentrated sulfuric acid is added to a solution of 0.2 g (0.87 mmol) of 5-trifluoromethyl-pyrrolo[3,2-b]pyridine-2-carboxylic acid, obtained in step 19.2, in 10 ml of ethanol. The solution is refluxed for 20 hours and then cooled and concentrated under reduced pressure. The resulting residue is then taken up in 50 ml of dichloromethane and washed successively with 20 ml of saturated aqueous sodium hydrogen carbonate solution, 40 ml of water and 20 ml of saturated aqueous sodium chloride solution, dried over sodium sulfate and then concentrated under reduced pressure. 0.19 g of product is obtained, and is used without further purification in the following step.

19.4 ethyl 1-(3-fluorobenzyl)-5-trifluoromethylpyrrolo[3,2-b]pyridine-2-carboxylate To a solution of 0.2 g (0.77 ml) of ethyl 5-trifluoromethylpyrrolo[3,2-b]pyridine-2-carboxylate, obtained in step 19.3, in 120 ml of dry tetrahydrofuran, maintained at 0° C. under argon, are successively added 0.13 ml (1.16 mmol) of 3-fluorobenzyl alcohol, 0.3 g (1.16 mmol) of triphenylphosphine and then 0.2 g (1.16 mmol) of diethyl azodicarboxylate. The reaction mixture is stirred for 20 hours at 20° C. and then concentrated under reduced pressure. The resulting residue is purified by chromatography on a column of silica (eluents: heptane/ethyl acetate). 0.21 g of the expected product is thus isolated in the form of a yellow oil.

19.5 N-(1,2-dimethyl-1H-benzimidazol-5-yl)-5-trifluoromethyl-1-[(3-fluorophenyl)methyl]-1H-pyrrolo[3,2-b]pyridine-2-carboxamide (Compound 24)

0.097 g (0.6 mmol) of 5-amino-1,2-dimethylbenzimidazole and 5 ml of dry toluene are placed, while flushing with nitrogen, in a 100 ml three-necked flask cooled to 0° C. and equipped with a magnetic stirrer. 0.41 ml (0.59 mmol) of a 2M solution of trimethylaluminum in toluene is then added slowly to this solution. The reaction mixture obtained is maintained under a nitrogen atmosphere and stirred, while allowing the temperature to rise gradually to 70° C. At this temperature, a solution of 0.2 g (0.55 mmol) of ethyl 1-(3-fluorobenzyl)-5-trifluoromethylpyrrolo[3,2-b]pyridine-2-carboxylate, obtained in step 19.4, in 10 ml of dry toluene is added dropwise over 5 minutes. The reaction mixture is then refluxed for 18 hours. 20 ml of cold water are then added to the solution cooled to 0° C. After stirring for 90 minutes, the solution is extracted three times with ethyl acetate (3×50 ml) and the combined organic phases are successively washed with 20 ml of saturated aqueous sodium hydrogen carbonate solution, 40 ml of water and 20 ml of saturated aqueous sodium chloride solution, dried over sodium sulfate and then concentrated under reduced pressure.

The resulting solid is triturated from boiling isopropyl ether to give, after drying, 97 mg of the expected product in the form of a pale yellow powder.

Melting point: 249-251° C.

$^1$H NMR (DMSO D$_6$), δ (ppm): 10.6 (s, 1H); 8.3 (d, 1H); 7.91 (s, 1H); 7.75 (d, 1H); 7.61 (s, 1H); 7.49 (m, 2H); 7.31 (m, 1H); 7.01 (m, 3H); 5.95 (s, 2H); 3.72 (s, 3H); 2.48 (s, 3H).

Tables 1 and 2 below illustrate the chemical structures and the physical properties of a number of compounds of general formula (I) according to the invention. Table 1 illustrates compounds of general formula (I) in which the pyrrolopyridine nucleus is an optionally substituted pyrrolo[2,3-c]pyridine. Table 2 illustrates compounds of general formula (I) in which the pyrrolopyridine nucleus is an optionally substituted pyrrolo[2,3-b]pyridine. Table 3 illustrates compounds of general formula (I) in which the pyrrolopyridine nucleus is an optionally substituted pyrrolo[3,2-c]pyridine. Table 4 illustrates compounds of general formula (I) in which the pyrrolopyridine nucleus is an optionally substituted pyrrolo[3,2-b]pyridine.

In these tables:
the "m.p." column gives the melting points of the products in degrees Celsius (° C.);
in the "salt" column, "–" represents a compound in free base form, whereas "HCl" represents a compound in hydrochloride form, and the ratio in parentheses is the (acid:base) ratio;
Ph represents a phenyl group.

TABLE 1

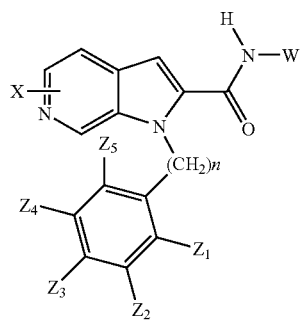

(I)

| No. | X | n | $Z_1, Z_2, Z_3, Z_4, Z_5$ | W | Salt | m.p. (°C.) |
|---|---|---|---|---|---|---|
| 1 | H | 1 | H, F, H, H, H | 1-methyl-indol-5-yl | — | 213-214.5 |
| 2 | 5-F | 1 | H, F, H, H, H | 1-methylbenzimidazol-5-yl | — | 279-281 |
| 3 | 5-Cl | 1 | H, F, H, H, H | 1,2-dimethyl-benzimidazol-5-yl | — | 240-242 |
| 4 | H | 1 | H, F, H, H, H | 1,2-dimethyl-benzimidazol-5-yl | HCl (2:1) | 309-310 |
| 5 | 5-F | 1 | H, F, H, H, H | 2-methylbenzothiazol-5-yl | — | 193-195 |
| 6 | 5-F | 1 | H, F, H, H, H | 1,2-dimethyl-benzimidazol-5-yl | — | 245-247 |
| 7 | 5-Ph | 1 | H, F, H, H, H | 1,2-dimethyl-benzimidazol-5-yl | — | 288-290 |

TABLE 3

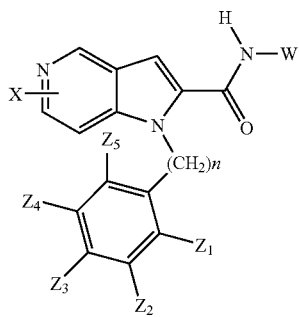

(I)

| No. | X | n | $Z_1, Z_2, Z_3, Z_4, Z_5$ | W | Salt | m.p. (°C.) |
|---|---|---|---|---|---|---|
| 22 | H | 1 | H, F, H, H, H | 1,2-dimethyl-benzimidazol-5-yl | — | 263-264 |

TABLE 2

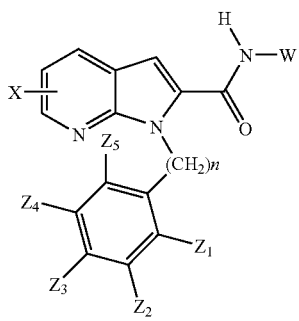

(I)

| No. | X | n | $Z_1, Z_2, Z_3, Z_4, Z_5$ | W | Salt | m.p. (°C.) |
|---|---|---|---|---|---|---|
| 8 | H | 1 | H, F, H, H, H | 1-methylindol-5-yl | — | 191-191.5 |
| 9 | H | 1 | H, F, H, H, H | 1-methylbenzimidazol-5-yl | HCl (3:2) | 171-177 |
| 10 | H | 1 | H, F, H, H, H | 2-oxo-1,2,3,4-tetrahydroquinol-7-yl | — | 280-282 |
| 11 | H | 1 | H, F, H, H, H | quinol-7-yl | HCl (1:1) | 260-262 |
| 12 | H | 1 | H, H, H, H, H | 1-methylindol-5-yl | — | 181-182 |
| 13 | H | 2 | H, H, H, H, H | 1-methylindol-5-yl | — | 196-199 |
| 14 | H | 1 | H, F, H, H, H | 2-methylbenzothiazol-5-yl | HCl (3:2) | 211-212 |
| 15 | 5-F | 1 | H, F, H, H, H | 1-methylbenzimidazol-5-yl | — | 266-268 |
| 16 | 5-$CF_3$ | 1 | H, F, H, H, H | 1,2-dimethylbenzimidazol-5-yl | — | 263-265 |
| 17 | 5-$CF_3$ | 1 | H, F, H, H, H | 1-methylindol-5-yl | — | 229-231 |
| 18 | 5-$CF_3$ | 1 | H, F, H, H, H | 2-methylbenzothiazol-5-yl | — | 204-206 |
| 19 | H | 1 | H, F, H, H, H | 1,2-dimethylbenzimidazol-5-yl | — | 242-244 |
| 20 | 5-F | 1 | H, F, H, H, H | 1,2-dimethylbenzimidazol-5-yl | — | 226-228 |
| 21 | H | 0 | H, H, H, H, H | 1,2-dimethylbenzimidazol-5-yl | — | 286-288 |

TABLE 4

(I)

[Chemical structure of formula (I) showing a pyrrolopyridine-carboxamide with substituents X, Z$_1$-Z$_5$, W, n, and (CH$_2$)$_n$ linker to a benzene ring]

| No. | X | n | $Z_1, Z_2, Z_3, Z_4, Z_5$ | W | Salt | m.p. (°C.) |
|---|---|---|---|---|---|---|
| 23 | H | 1 | H, F, H, H, H | 1-methylbenzimidazol-5-yl | — | 277-281 |
| 24 | 5-CF$_3$ | 1 | H, F, H, H, H | 1,2-dimethylbenzimidazol-5-yl | — | 249-251 |
| 25 | H | 1 | H, F, H, H, H | 2-methylbenzothiazol-5-yl | — | 263-265 |
| 26 | H | 1 | H, F, H, H, H | 1,2-dimethylbenzimidazol-5-yl | — | 245-247 |

The compounds of the invention were subjected to in vitro and in vivo pharmacological tests that demonstrated their value as substances with therapeutic activities.

Test of Inhibition of the Current Induced with Capsaicin on Rat DRGs

Primary Culture of Rat Dorsal Root Ganglion (DRG) Cells:

The neurons of the DRG naturally express the TRPV1 receptor.

The primary cultures of newborn rat DRGs are prepared using 1-day-old rats. Briefly, after dissection, the ganglions are trypsinized and the cells dissociated by mechanical trituration. The cells are resuspended in an Eagle basal culture medium containing 10% fetal calf serum, 25 mM KCl, 2 mM glutamine, 100 μg/ml gentamicin and 50 ng/ml of NGF, and then deposited on glass slides coated with laminin (0.25×10$^6$ cells per slide), which are then placed in Corning 12-well dishes. The cells are incubated at 37° C. in a humidified atmosphere containing 5% CO$_2$ and 95% air. Cytosine β-D-arabinoside (1 μM) is added 48 hours after culturing, to prevent the growth of non-neuronal cells. The slides are transferred into experimental chambers for the patch-clamp studies after 7-10 days of culturing.

Electrophysiology:

The measuring chambers (volume 800 μl) containing the cell preparation are placed on the platform of an inverted microscope (Olympus IMT2) equipped with Hoffman optics (Modulation Contrast, New York) and observed at a magnification of 400×. The chambers are continuously gravity-influxed (2.5 ml/min) using a solution distributor accepting 8 inlets and whose sole outlet, consisting of a polyethylene tube (aperture 500 μm), is placed less than 3 mm from the cell under study. The "whole cell" configuration of the patch-clamp technique was used. The borosilicate glass pipettes (resistance 5-10 MOhms) are brought to the cell by means of a 3D piezoelectric micromanipulator (Burleigh, PC1000). The overall currents (membrane potential set at −60 mV) are recorded with an Axopatch 1D amplifier (Axon Instruments, Foster city, Calif.), connected to a PC running the Pclamp8 software (Axon Instrument). The current plots are recorded on paper and simultaneously digitized (sampling frequency 15 to 25 Hz) and acquired on the hard drive of the PC.

The application of a 300 nM capsaicin solution induces on the DRG cells (voltage set at −70 mV) an entering cationic current. In order to minimize the desensitization of the receptors, a minimum interval of one minute between two applications of capsaicin is observed. After a control period (stabilization of the capsaicin response alone), the test compounds are applied alone at a given concentration (concentration of 10 nM or 1 nM) for a time of 4 to 5 minutes, during which several capsaicin+compound tests are performed (to obtain the maximum inhibition). The results are expressed as a percentage of inhibition of the control capsaicin response.

The percentages of inhibition of the capsaicin response (300 nM) are between 20% and 100% for the most active compounds of the invention tested at concentrations of 0.1 to 10 nM. The compounds of the invention are thus effective in vitro antagonists of receptors of TRPV1 type.

Test of Mouse Corneal Irritation

The irritant nature of capsaicin is readily assessed on the cornea since this organ is one of the organs most densely innervated with C fibres. In this context, from preliminary experiments, the application of a very small amount of capsaicin (2 μl at a concentration of 160 μM) to the surface of the cornea of an animal leads to a certain number of stereotypical behavioral traits associated with irritation, which are easy to record. Among these, the following are noted: blinking of the eye, rubbing of the instilled eye with the ipsilateral front paw, rubbing of the face with both front paws, scratching of the ipsilateral face with the hind paw. The duration of this behavior does not exceed the 2 minutes of observation, and the animal then resumes its normal activity. Its aspect is moreover also normal. The mouse is not recluse in a corner with raised hackles and does not develop any observable sign of suffering. It may be concluded therefrom that the duration of action of capsaicin at these doses is less than 2 minutes.

Summary of the Methodology:

The principle of the series of experiments is to determine whether the compounds of the invention can influence the behavioral response induced with a given amount of capsaicin. The capsaicin is initially diluted to 25 mM in DMSO and diluted, for its final use, in Tween 80 to 10% in physiological saline. It appears, from control studies, that, under these conditions, the solvent has no effect.

In practice, the test product is administered orally and, with a delay (pretreatment time: t) that depends on the pharmacokinetic data, the animal receives an ocular instillation of 2 μl of a 160 μM capsaicin solution prepared as indicated above. During a 2-minute observation following the instillation, the number of times the instilled eye is rubbed with the ipsilateral front paw is recorded.

For a given animal, the percentage of protection is calculated as follows:

$P = 100 - ((\text{number of scratching actions observed}/\text{mean number of scratching actions for the group treated with the solvent}) \times 100)$ This percentage of protection is averaged for each group of animals (n=number of animals tested with the compound of the invention).

The percentages of protection evaluated in this model for the most active compounds of the invention, used at doses of 1 to 10 mg/kg (po), are between 20% and 100% (see the example in Table 5).

TABLE 5

| Compound No. | % P - (t) at 1 mg/kg (po) - (n = 10) |
|---|---|
| 15 | 50% - (1 h) |

The results of these tests show that the most active compounds of the invention block the effects induced by stimulation of the TRPV1 receptors.

The compounds of the invention may thus be used for the preparation of medicaments, especially for the preparation of a medicament for preventing or treating pathologies in which the TRPV1 receptors are involved.

Thus, according to another of its aspects, a subject of the invention is medicaments that comprise a compound of formula (I), or a pharmaceutically acceptable salt, or alternatively a hydrate or a solvate of the said compound.

These medicaments find their therapeutic use especially in the prevention and/or treatment of pain and inflammation, chronic pain, neuropathic pain (trauma-related, diabetic, metabolic, infection-related or toxic pain, or pain induced by an anticancer or iatrogenic treatment), (osteo)arthritic pain, rheumatic pain, fibromyalgia, back pain, cancer-related pain, facial neuralgia, headaches, migraine, dental pain, burns, sunburn, animal bites or insect bites, post-herpetic neuralgia, muscular pain, trapped nerves (central and/or peripheral), spinal column and/or brain trauma, ischemia (of the spinal column and/or the brain), neurodegeneration, hemorrhagic strokes (of the spinal column and/or of the brain) and post-stroke pain.

The compounds of the invention may be used for the preparation of a medicament for preventing and/or treating urological disorders such as hyperactivity of the bladder, vesical hyperreflexia, vesical instability, incontinence, urgent micturition, urinary incontinence, cystitis, nephritic colic, pelvic hypersensitivity and pelvic pain.

The compounds of the invention may be used to prepare a medicament for preventing and/or treating gynecological disorders, for instance vulvodynia and pain associated with salpingitis or with dysmenorrhea.

These products may also be used for the preparation of a medicament for preventing and/or treating gastrointestinal disorders such as gastroesophageal reflux disorder, stomach ulcers, duodenal ulcers, functional dyspepsia, colitis, IBS, Crohn's disease, pancreatitis, oesophagitis and biliary colic.

The compounds of the invention may also be used for preparation of a medicament for treating diabetes.

Similarly, the products of the present invention may be useful in the prevention and/or treatment of respiratory disorders such as asthma, coughing, COPD, bronchoconstriction and inflammatory disorders. These products may also be used for preventing and/or treating psoriasis, pruritus, dermal, ocular or mucous irritation, herpes and zona.

The compounds of the invention may also be used for the preparation of a medicament for treating depression.

According to another of its aspects, the present invention relates to pharmaceutical compositions comprising a compound according to the invention as active principle. These pharmaceutical compositions contain an effective dose of at least one compound according to the invention, or a pharmaceutically acceptable salt, a hydrate or solvate of the said compound, and also at least one pharmaceutically acceptable excipient.

The said excipients are chosen, according to the pharmaceutical form and the desired mode of administration, from the usual excipients known to those skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or the possible salt, solvate or hydrate thereof, may be administered in a unit administration form, as a mixture with standard pharmaceutical excipients, to man and animals for the prophylaxis or treatment of the disorders or diseases mentioned above.

The appropriate unit forms of administration include oral forms such as tablets, soft or hard gel capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms and implants. For topical application, the compounds according to the invention may be used in creams, gels, pomades or lotions.

By way of example, a unit form of administration of a compound according to the invention in tablet form may comprise the following components:

| | |
|---|---|
| Compound according to the invention | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

The said unit forms are dosed to allow a daily administration of from 0.001 to 30 mg of active principle per kg of body weight, according to the galenical form.

There may be particular cases in which higher or lower dosages are appropriate: such dosages do not depart from the scope of the invention. According to the usual practice, the dosage that is appropriate for each patient is determined by the doctor according to the mode of administration, the weight and the response of the said patient.

According to another of its aspects, the present invention also relates to a method for treating the pathologies indicated above, which comprises the administration to a patient of an effective dose of a compound according to the invention, or a pharmaceutically acceptable salt, or hydrate or solvate thereof.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A compound of the formula (I)

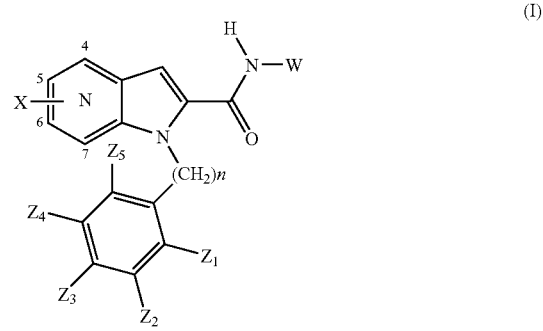

wherein:

n is equal to 0, 1, 2 or 3;

the pyrrolopyridine nucleus is a pyrrolo[3,2-b]pyridine group, a pyrrolo[3,2-c]pyridine group, a pyrrolo[2,3-c]pyridine group or a pyrrolo[2,3-b]pyridine group;

X is chosen from a halogen atom and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_1$-$C_6$-fluoroalkoxyl, cyano, C(O)NR$_1$R$_2$, nitro, NR$_1$R$_2$, $C_1$-$C_6$-thioalkyl, —S(O)—$C_1$-$C_6$-alkyl, —S(O)$_2$—$C_1$-$C_6$-alkyl, SO$_2$NR$_1$R$_2$, NR$_3$COR$_4$, NR$_3$SO$_2$R$_5$ or aryl group, the aryl being optionally substituted with one or more substituents chosen from a halogen and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_1$-$C_6$-fluoroalkoxyl, nitro or cyano group;

$Z_1$, $Z_2$, $Z_3$, $Z_4$ and $Z_5$ represent, independently of each other, a hydrogen or halogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_1$-$C_6$-fluoroalkoxyl, cyano, C(O)NR$_1$R$_2$, nitro, NR$_1$R$_2$, $C_1$-$C_6$-thioalkyl, —S(O)—$C_1$-$C_6$-alkyl, —S(O)$_2$—$C_1$-$C_6$-alkyl, SO$_2$NR$_1$R$_2$, NR$_3$COR$_4$, NR$_3$SO$_2$R$_5$, aryl-$C_1$-$C_6$-alkylene or aryl group, the aryl and the aryl-$C_1$-$C_6$-alkylene being optionally substituted with one or more substituents chosen from a halogen and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_1$-$C_6$-fluoroalkoxyl, nitro or cyano group; and wherein $R_1$ and $R_2$ represent, independently of each other, a hydrogen atom or a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene or aryl group; or $R_1$ and $R_2$ together forming, with the nitrogen atom that bears them, an azetidine, pyrrolidine, piperidine, azepine, morpholine, thiomorpholine, piperazine, homopiperazine group, this group being optionally substituted with a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene or aryl group;

$R_3$ and $R_4$ represent, independently of each other, a hydrogen atom or a $C_1$-$C_6$-alkyl, aryl-$C_1$-$C_6$-alkylene or aryl group;

$R_5$ represents a $C_1$-$C_6$-alkyl or aryl group; and

W represents a fused bicyclic group of formula:

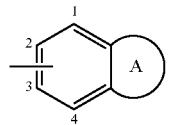

bonded to the nitrogen atom via positions 1, 2, 3 or 4; wherein

A represents a 5- to 7-membered heterocycle comprising from one to three heteroatoms chosen from O, S and N;

the carbon atom(s) of A being optionally substituted with one or more groups chosen from a hydrogen atom and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl, aryl-$C_1$-$C_6$-alkylene, oxo or thio group; and the nitrogen atom(s) of A being optionally substituted with $R_6$ when the nitrogen is adjacent to a carbon atom substituted with an oxo group, or with $R_7$ in the other cases; wherein $R_6$ represents a hydrogen atom or $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-$C_1$-$C_6$-alkylene or aryl group;

$R_7$ represents a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-$C_1$-$C_6$-alkylene, $C_1$-$C_6$-alkyl-C(O)—, $C_3$-$C_7$-cycloalkyl-$C_1$-$C_3$-alkylene-(CO)—, $C_1$-$C_6$-fluoroalkyl-C(O)—, $C_3$-$C_7$-cycloalkyl-C(O)—, aryl-C(O)—, aryl-$C_1$-$C_6$-alkylene-C(O)—, $C_1$-$C_6$-alkyl-S(O)$_2$—, $C_1$-$C_6$-fluoroalkyl-S(O)$_2$—, $C_3$-$C_7$-cycloalkyl-S(O)$_2$—, $C_3$-$C_7$-cycloalkyl-$C_1$-$C_3$-alkylene-S(O)$_2$—, aryl-S(O)$_2$— or aryl-$C_1$-$C_6$-alkylene-S(O)$_2$— or aryl group;

the sulfur atom(s) of the heterocycle A possibly being in oxidized form;

the nitrogen atom(s) of the heterocycle A possibly being in oxidized form; and the nitrogen atom in position 4, 5, 6 or 7 of the pyrrolopyridine may be in oxidized form; or an acid-addition salt, thereof.

2. The compound of formula (I) according to claim 1, wherein n is equal to 1 or 2, or an acid-addition salt, thereof.

3. The compound of formula (I) according to claim 1, wherein the pyrrolopyridine nucleus is a pyrrolo[3,2-b]pyridine group, a pyrrolo[3,2-c]pyridine group, a pyrrolo[2,3-c]pyridine group or a pyrrolo[2,3-b]pyridine group; and X is chosen from a hydrogen or halogen atom and a $C_1$-$C_6$-alkyl, $C_3$-$C_7$-cycloalkyl, $C_1$-$C_6$-fluoroalkyl, $C_1$-$C_6$-alkoxyl, $C_1$-$C_6$-fluoroalkoxyl, nitro, NR$_1$R$_2$, $C_1$-$C_6$-thioalkyl, —S(O)—$C_1$-$C_6$-alkyl, —S(O)$_2$—$C_1$-$C_6$-alkyl, or aryl group; wherein $R_1$ and $R_2$ are hydrogen atom;

or an acid-addition salt, thereof.

4. The compound of formula (I) according to claim 2, wherein the pyrrolopyridine nucleus is a pyrrolo[3,2-b]pyridine group, a pyrrolo[3,2-c]pyridine group, a pyrrolo[2,3-c]pyridine group or a pyrrolo[2,3-b]pyridine group; and X is chosen from a hydrogen or halogen atom, a $C_1$-$C_6$-alkyl, $C_3$-$C_7$-cycloalkyl, $C_1$-$C_6$-fluoroalkyl, $C_1$-$C_6$-alkoxyl, $C_1$-$C_6$-fluoroalkoxyl, nitro, NR$_1$R$_2$, $C_1$-$C_6$-thioalkyl, —S(O)—$C_1$-$C_6$-alkyl, —S(O)$_2$—$C_1$-$C_6$-alkyl, or aryl group;

wherein $R_1$ and $R_2$ are hydrogen atom;

or an acid-addition salt, thereof.

5. The compound of formula (I) according to claim 1, wherein the pyrrolopyridine nucleus is a pyrrolo[3,2-b]pyridine group, a pyrrolo[3,2-c]pyridine group, a pyrrolo[2,3-c]pyridine group or a pyrrolo[2,3-b]pyridine group; and X is chosen from a halogen atom, a $C_1$-$C_6$-fluoroalkyl or aryl group;

or an acid-addition salt, thereof.

6. The compound of formula (I) according to claim 2, wherein the pyrrolopyridine nucleus is a pyrrolo[3,2-b]pyridine group, a pyrrolo[3,2-c]pyridine group, a pyrrolo[2,3-c]pyridine group or a pyrrolo[2,3-b]pyridine group; and X is chosen from a halogen atom, a $C_1$-$C_6$-fluoroalkyl or aryl group;

or an acid-addition salt, thereof.

7. The compound of formula (I) according to claim 1, wherein $Z_1$, $Z_2$, $Z_3$, $Z_4$ and $Z_5$ represent, independently of each other, a hydrogen or halogen atom;

or an acid-addition salt, thereof.

8. The compound of formula (I) according to claim 1, wherein W is chosen from indolinyl, indolyl, isoindolyl, isoindolinyl, benzofuranyl, dihydrobenzofuranyl, benzothiophenyl, dihydrobenzothiophenyl, benzoxazolyl, dihydrobenzoxazolinyl, isobenzofuranyl, dihydroisobenzofuranyl, benzimidazolyl, dihydrobenzimidazolyl, indazolyl, benzothiazolyl, isobenzothiazolyl, dihydroisobenzothiazolyl, benzotriazolyl, quinolyl, dihydroquinolyl, tetrahydroquinolyl, isoquinolyl, dihydroisoquinolyl, tetrahydroisoquinolyl, benzoxazinyl, dihydrobenzoxazinyl, benzothiazinyl, dihydrobenzothiazinyl, cinnolinyl, quinazolinyl, dihydroquinazolinyl, tetrahydroquinazolinyl, quinoxalinyl, dihydroquinoxalinyl, tetrahydroquinoxalinyl, phthalazinyl, dihydrophthalazinyl, tetrahydrophthalazinyl, tetrahydrobenz[b]azepinyl, tetrahydrobenz[c]azepinyl, tetrahydrobenz[d]azepinyl, tetrahydrobenzo[b][1,4]diazepinyl, tetrahydrobenzo[e][1,4]diazepinyl, tetrahydrobenzo[b][1,4]oxazepinyl or tetrahydrobenzo[b][1,4]thiazepinyl groups;
and wherein
the carbon or nitrogen atom(s) of said group W being optionally substituted as defined in the general formula (I) according to claim 1;
or an acid-addition salt, thereof.

9. The compound of formula (I) according to claim 1, wherein W represents a fused bicyclic group of formula:

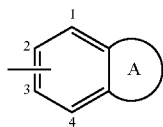

bonded to the nitrogen atom via positions 1, 2, 3 or 4; wherein
A represents a 5- to 7-membered heterocycle comprising from one to three heteroatoms chosen from O, S and N;
the carbon atom(s) of A being optionally substituted with one or more groups chosen from a hydrogen atom and a $C_1$-$C_6$-alkyl or an oxo group; or
the nitrogen atom(s) of A being optionally substituted with $R_6$ when the nitrogen is adjacent to a carbon atom substituted with an oxo group, or with $R_7$ in the other cases; wherein
$R_6$ represents a hydrogen atom;
$R_7$ represents a hydrogen atom or a $C_1$-$C_6$-alkyl group;
or an acid-addition salt, thereof.

10. The compound of formula (I) according to claim 1, wherein W is chosen from indolyl, benzimidazolyl, tetrahydroquinolyl, quinolyl or benzothiazolyl;
or an acid-addition salt, thereof.

11. A process for preparing a compound of formula (I) according to claim 1, comprising:
reacting a compound of formula (IV)

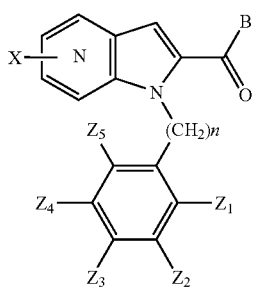

wherein X, $Z_1$, $Z_2$, $Z_3$, $Z_4$, $Z_5$ and n are as defined in claim 1 and B represents a $C_1$-$C_4$-alkoxy group,
with an amide of the compound of formula (V)

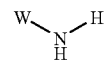

wherein W is as defined in claim 1,
at the reflux point of a solvent, the amide of the compound of formula (V) being prepared first by reacting the compound of formula (V) with trimethylaluminum.

12. A process for preparing a compound of formula (I) according to claim 1, comprising:
reacting a compound of formula (IV)

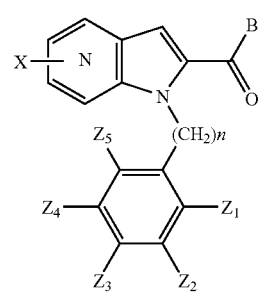

wherein X, $Z_1$, $Z_2$, $Z_3$, $Z_4$, $Z_5$ and n are as defined in claim 1 and B represents a hydroxyl group,
with thionyl chloride at the reflux point of a solvent to form an acid chloride of formula (IV) wherein B represents a chlorine atom; and
reacting a compound of formula (IV) thus obtained, in which X, $Z_1$, $Z_2$, $Z_3$, $Z_4$, $Z_5$ and n are as defined in claim 1 and B represents a chlorine atom, in the presence of a base, with the compound of general formula (V),

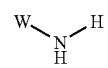

wherein W is as defined in claim 1; or
performing a coupling reaction between a compound of formula (IV), in which X, $Z_1$, $Z_2$, $Z_3$, $Z_4$, $Z_5$ and n are as defined in claim 1 and B represents a hydroxyl group,
and the compound of formula (V), in which W is as defined in claim 1, in the presence of a coupling agent and a base, in a solvent.

13. A pharmaceutical composition comprising a compound of formula (I) according to claim 1 or a pharmaceutically acceptable salt, thereof in combination with at least one pharmaceutically acceptable excipient.

14. A pharmaceutical composition comprising a compound of formula (I) according to claim 2 or a pharmaceutically acceptable salt, thereof in combination with at least one pharmaceutically acceptable excipient.

15. A pharmaceutical composition comprising a compound of formula (I) according to claim 3 or a pharmaceutically acceptable salt, thereof in combination with at least one pharmaceutically acceptable excipient.

16. A pharmaceutical composition comprising a compound of formula (I) according to claim 4 or a pharmaceutically acceptable salt, thereof in combination with at least one pharmaceutically acceptable excipient.

17. A pharmaceutical composition comprising a compound of formula (I) according to claim 5 or a pharmaceutically acceptable salt, thereof in combination with at least one pharmaceutically acceptable excipient.

18. A pharmaceutical composition comprising a compound of formula (I) according to claim 6 or a pharmaceutically acceptable salt, thereof in combination with at least one pharmaceutically acceptable excipient.

19. A pharmaceutical composition comprising a compound of formula (I) according to claim 7 or a pharmaceutically acceptable salt, thereof in combination with at least one pharmaceutically acceptable excipient.

20. A pharmaceutical composition comprising a compound of formula (I) according to claim 8 or a pharmaceutically acceptable salt, thereof in combination with at least one pharmaceutically acceptable excipient.

21. A pharmaceutical composition comprising a compound of formula (I) according to claim 9 or a pharmaceutically acceptable salt, thereof in combination with at least one pharmaceutically acceptable excipient.

22. A pharmaceutical composition comprising a compound of formula (I) according to claim 10 or a pharmaceutically acceptable salt, thereof in combination with at least one pharmaceutically acceptable excipient.

* * * * *

UNITED STATES PATENT AND TRADEMARK OFFICE
CERTIFICATE OF CORRECTION

| | |
|---|---|
| PATENT NO. | : 7,763,636 B2 |
| APPLICATION NO. | : 11/970886 |
| DATED | : July 27, 2010 |
| INVENTOR(S) | : Laurent Dubois et al. |

It is certified that error appears in the above-identified patent and that said Letters Patent is hereby corrected as shown below:

In column 3, line 2, delete "dihydroisoquinolyi," and insert -- dihydroisoquinolyl, --, therefor.

In column 5, line 27, delete "C(O)NR$^1$R$_2$," and insert -- C(O)NR$_1$R$_2$, --, therefor.

In column 12, line 15-20, in 2$^{nd}$ Structure, delete " 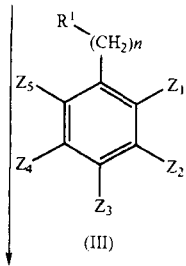 " and insert -- 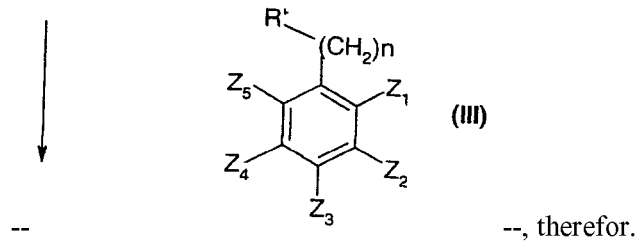 --, therefor.

Signed and Sealed this
Sixteenth Day of August, 2011

David J. Kappos
*Director of the United States Patent and Trademark Office*